(12) United States Patent
Lee et al.

(10) Patent No.: US 7,592,454 B2
(45) Date of Patent: *Sep. 22, 2009

(54) SUBSTITUTED HEXAHYDRO-PYRIDOINDOLE DERIVATIVES AS SEROTONIN RECEPTOR AGONISTS AND ANTAGONISTS

(75) Inventors: Taekyu Lee, Doylestown, PA (US); Wei Deng, Lexington, MA (US); Albert J. Robichaud, Ringoes, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 621 days.

This patent is subject to a terminal disclaimer.

(21) Appl. No.: 11/104,933

(22) Filed: Apr. 13, 2005

(65) Prior Publication Data

US 2005/0239768 A1    Oct. 27, 2005

Related U.S. Application Data

(60) Provisional application No. 60/562,186, filed on Apr. 14, 2004.

(51) Int. Cl.
*C07D 471/04* (2006.01)
*A61K 31/437* (2006.01)
(52) U.S. Cl. ........................ 546/84; 514/292
(58) Field of Classification Search ................ 546/79, 546/84; 514/292
See application file for complete search history.

(56) References Cited

U.S. PATENT DOCUMENTS

| 2002/0107278 A1 | 8/2002 | Frank et al. |
| 2003/0060464 A1 | 3/2003 | Ennis et al. |
| 2004/0180875 A1 | 9/2004 | Lee et al. |

OTHER PUBLICATIONS

Dorwald F. A. Side Reactions in Organic Synthesis, 2005, Wiley: VCH, Weinheim p. IX of Preface.*
U.S. Appl. No. 10/743,449, filed Dec. 19, 2003, Lee et al.

Curzon, G., et al., "*m*-CPP: a tool for studying behavioural responses associated with 5-HT$_{1c}$ receptors", TiPS (Trends in Pharmacological Sciences), vol. 11, pp. 181-182, 1990.
Leonard, B.E., "The Comparative Pharmacology of New Antidepressants", J. Clin. Psychiatry, 54:8 (suppl), pp. 3-17, 1993.
Ugedo, L., et al., "Ritanserin, a 5-HT$_2$ receptor antagonist, activates midbrain dopamine neurons by blocking serotonergic inhibition", Psychopharmacology, vol. 98, pp. 45-50, 1989.
Hartig, P.R., et al., "The 5-HT$_{1c}$ Receptor", Annals of the New York Academy of Sciences, vol. 600, pp. 149-166, 1990.
Berendsen, H.H.G., et al., "Involvement of 5-HT$_{1c}$-receptors in drug-induced penile erections in rats", Psychopharmacology, vol. 101, pp. 57-61, 1990.
Koek, W., et al., "Behavioral Pharmacology of Antagonists at 5-HT$_2$/5-HT$_{1c}$ Receptors", Neuroscience & Biobehavioral Reviews, vol. 16, pp. 95-105, 1992.

* cited by examiner

*Primary Examiner*—Rita J Desai
(74) *Attorney, Agent, or Firm*—Maureen S. Gibbons; Hong Liu

(57) ABSTRACT

The present application provides novel compounds according to Formula (I):

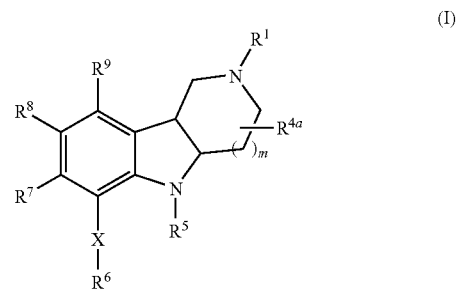

including all stereoisomers, solvates, prodrug esters and pharmaceutically acceptable salt forms thereof, wherein $R^1$, $R^{4a}$, $R^5$, $R^6$, $R^7$, $R^8$, $R^9$, m, and X are described herein. Additionally, the present application provides novel pharmaceutical compositions comprising at least one compound according to Formula (I). Further, the present application provides methods of treating a patient in need comprising administering a therapeutically effective amount of at least one compound according to Formula (I).

7 Claims, No Drawings

SUBSTITUTED HEXAHYDRO-PYRIDOINDOLE DERIVATIVES AS SEROTONIN RECEPTOR AGONISTS AND ANTAGONISTS

RELATED APPLICATIONS

This application claims priority benefit under Title 35 § 119(e) of U.S. provisional Application No. 60/562,186, filed Apr. 14, 2004, the contents of which are herein incorporated by reference.

BACKGROUND OF THE INVENTION

There exists a substantial correlation for the relationship between 5-HT2 receptor modulation and a variety of diseases and therapies. To date, three subtypes of the 5-HT2 receptor class have been identified, 5-HT2A, 5-HT2B, and 5-HT2C. Prior to the early 1990's the 5-HT2C and 5-HT2A receptors were referred to as 5-HT1C and 5-HT2, respectively.

The agonism or antagonism of 5-HT2 receptors, either selectively or nonselectively, has been associated with the treatment of various central nervous system (CNS) disorders. Ligands possessing affinity for the 5-HT2 receptors have been shown to have numerous physiological and behavioral effects (Trends in Pharmacological Sciences, 11, 181, 1990). In the recent past the contribution of serotonergic activity to the mode of action of antidepressant drugs has been well documented. Compounds that increase the overall basal tone of serotonin in the CNS have been successfully developed as antidepressants. The serotonin selective reuptake inhibitors (SSRI) function by increasing the amount of serotonin present in the nerve synapse. These breakthrough treatments, however, are not without side effects and suffer from delayed onset of action (Leonard, J. Clin. Psychiatry, 54 (suppl.), 3, 1993). Due to the mechanism of action of the SSRIs, they effect the activity of a number of serotonin receptor subtypes. This non-specific modulation of the serotonin family of receptors most likely plays a significant role in the side effect profile. In addition, these compounds often have a high affinity for a number of the serotonin receptors as well as a multitude of other monoamine neurotransmitters and nuisance receptors. Removing some of the receptor cross reactivity would allow for the examination and possible development of potent therapeutic ligands with an improved side effect profile.

There is ample evidence to support the role of selective 5-HT2 receptor ligands in a number of disease therapies. Modulation of 5-HT2 receptors has been associated with the treatment of schizophrenia and psychoses (Ugedo, L., et al., Psychopharmacology, 98, 45, 1989). Mood, behavior and hallucinogenesis can be affected by 5-HT2 receptors in the limbic system and cerebral cortex. 5-HT2 receptor modulation in the hypothalamus can influence appetite, thermoregulation, sleep, sexual behavior, motor activity, and neuroendocrine function (Hartig, P., et.al., Annals New York Academy of Science, 149, 159). There is also evidence indicating that 5-HT2 receptors mediate hypoactivity, effect feeding in rats, and mediate penile erections (Psychopharmacology, 101, 57, 1990).

Compounds exhibiting selectivity for the 5-HT2B receptor are useful in treating conditions such as tachygastria, hypermotility associated with irritable bowel disorder, constipation, dyspepsia, and other peripherally mediated conditions.

5-HT2A antagonists have been shown to be effective in the treatment of schizophrenia, anxiety, depression, and migraines (Koek, W., Neuroscience and Behavioral reviews, 16, 95, 1996). Aside from the beneficial antipsychotic effects, classical neuroleptic are frequently responsible for eliciting acute extrapyramidal side effects and neuroendocrine disturbances. These compounds generally possess significant dopamine D2 receptor affinity (as well as other nuisance receptor affinity) which frequently is associated with extra pyramidal symptoms and tardive dyskinesia, thus detracting from their efficacy as front line treatments in schizophrenia and related disorders. Compounds possessing a more favorable selectivity profile would represent a possible improvement for the treatment of CNS disorders.

DETAILED DESCRIPTION OF THE INVENTION

The present application provides novel compounds according to Formula (I):

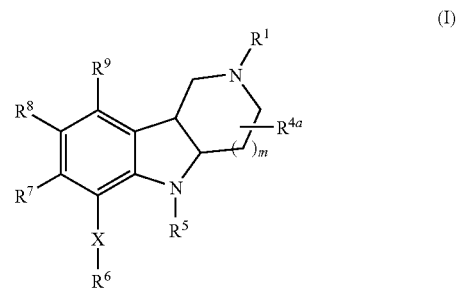

(I)

including all stereoisomers, solvates, prodrug esters and pharmaceutically acceptable salt forms thereof, wherein m, $R^1$, $R^{4a}$, $R^5$, $R^6$, $R^7$, $R^8$, $R^9$ and X are defined herein. Additionally, the present application provides novel pharmaceutical compositions comprising at least one compound according to Formula (I). Further, the present application provides methods of treating a patient in need comprising administering a therapeutically effective amount of at least one compound according to Formula (I).

DEFINITIONS

The compounds herein described may have asymmetric centers. Compounds of the present invention containing an asymmetrically substituted atom may be isolated in optically active or racemic forms. It is well known in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g. $R^2$, $R^{11}$, $R^{33}$, $R^{41}$, $R^{42}$ etc.) occurs more than one time in any constituent or formula for a compound, its definition at each occurrence is independent of its definition at every other occurrence. Thus, for example, if a group is shown to be substituted with 0-2 $R^2$, then said group may optionally be substituted with up to two $R^2$ groups and $R^2$ at each occurrence is selected independently from the definition of $R^2$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" or "alkylene" is intended to include both branched and straight-chain saturated aliphatic hydrocarbon groups having the specified number of carbon atoms; for example, "$C_1$-$C_6$ alkyl" or "$C_{1-6}$ alkyl" denotes alkyl having 1 to 6 carbon atoms. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

"Alkenyl" or "alkenylene" is intended to include hydrocarbon chains of either a straight or branched configuration having the specified number of carbon atoms, for example "$C_{2-6}$ alkenyl", and one or more unsaturated carbon-carbon bonds which may occur in any stable point along the chain. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either a straight or branched configuration, having the specified number of carbon atoms, for example "$C_{2-6}$ alkynyl", and one or more carbon-carbon triple bonds which may occur in any stable point along the chain, such as ethynyl, propynyl, butynyl, pentynyl, hexynyl and the like.

"Cycloalkyl" is intended to include saturated ring groups, having the specified number of carbon atoms. For example, "$C_3$-$C_6$ cycloalkyl" denotes such as cyclopropyl, cyclobutyl, cyclopentyl, or cyclohexyl.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Similarly, "alkylthio" is represents an alkyl group as defined above with the indicated number of carbon atoms attached through a sulpher bridge.

"Halo" or "halogen" as used herein refers to fluoro, chloro, bromo, and iodo; and "counterion" is used to represent a small, negatively charged species such as chloride, bromide, hydroxide, acetate, sulfate, and the like.

"Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, pentachloroethyl, 2,2,2-trifluoroethyl, heptafluoropropyl, and heptachloropropyl.

As used herein, "carbocycle" is intended to mean any stable 3- to 7-membered monocyclic or bicyclic or 7- to 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, or tetrahydronaphthyl (tetralin).

As used herein, the term "heterocycle" or "heterocyclic ring" or "heterocyclic ring system" is intended to mean a stable 5- to 7-membered monocyclic or bicyclic or 7- to 14-membered bicyclic heterocyclic ring which is saturated partially unsaturated or unsaturated (aromatic), and which consists of carbon atoms and 1, 2, 3 or 4 heteroatoms independently selected from the group consisting of N, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1.

Examples of heterocycles include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazalonyl, carbazolyl, 4aH-carbazolyl, b-carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, imidazolopyridinyl, 1H-indazolyl, indolenyl, indolinyl, indolizinyl, indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolopyridinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thiazolopyridinyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Preferred heterocycles include, but are not limited to, pyridinyl, furanyl, thienyl, pyrrolyl, pyrazolyl, pyrazinyl, piperazinyl, imidazolyl, indolyl, benzimidazolyl, 1H-indazolyl, oxazolidinyl, benzotriazolyl, benzisoxazolyl, benzoxazolyl, oxindolyl, benzoxazolinyl, benzthiazolyl, benzisothiazolyl, isatinoyl, isoxazolopyridinyl, isothiazolopyridinyl, thiazolopyridinyl, oxazolopyridinyl, imidazolopyridinyl, and pyrazolopyridinyl. Preferred 5 to 6 membered heterocycles include, but are not limited to, pyridinyl, furanyl, thienyl, pyrrolyl, pyrazolyl, pyrazinyl, piperazinyl, imidazolyl, and oxazolidinyl. Also included are fused ring and spiro compounds containing, for example, the above heterocycles.

As used herein, the term "bicyclic heterocyclic ring system" is intended to mean a stable 9- to 10-membered bicyclic heterocyclic ring formed from the substituent $NR^{12}R^{13}$, which is partially unsaturated or unsaturated (aromatic), and which consists of carbon atoms, a nitrogen atom, and 1 or 2 additional heteroatoms independently selected from the group consisting of N, O and S. The additional nitrogen or sulfur heteroatoms may optionally be oxidized. The heterocyclic ring is attached to its pendant group by the nitrogen atom of the group $NR^{12}R^{13}$ and for which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. The term "bicyclic heterocyclic ring system" is intended to be a subset of the term "heterocyclic ring system". Preferred examples of a 9- to 10-membered bicyclic heterocyclic ring system are benzimidazolyl, benzimidazolinyl, benzoxazolinyl, dihydrobenzthiazolyl, dihydrodioxobenzthiazolyl, benzisoxazolinyl, 1H-indazolyl, indolyl, indolinyl, isoindolinyl, tetrahydroisoquinolinyl, tetrahydro-quinolinyl, and benzotriazolyl.

Additionally, a subclass of preferred heterocycles are heterocycles which function as an isostere of a cyclic but non-heterocyclic substituent such as —$CH_2$—C(=O)-phenyl. Preferred examples of such heterocycles include, but are not limited to, benzimidazolyl, benzofuranyl, benzothiophenyl, benzoxazolyl, benzthiazolyl, benzisoxazolyl, furanyl, imidazolinyl, 1H-indazolyl, indolinyl, isoindolinyl, isoquinolinyl, oxazolyl, piperidinyl, pyrazinyl, pyridinyl, pyrimidinyl, quinolinyl, thiazolyl, thiophenyl, and 1,2,3-triazolyl.

As used herein, the term "aryl", or aromatic residue, is intended to mean an aromatic moiety containing six to ten carbon atoms, such as phenyl and naphthyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

"Prodrugs" are intended to include any covalently bonded carriers which release the active parent drug according to Formula (I) in vivo when such prodrug is administered to a mammalian subject. Prodrugs of a compound of Formula (I) are prepared by modifying functional groups present in the compound in such a way that the modifications are cleaved, either in routine manipulation or in vivo, to the parent compound. Prodrugs include compounds of Formula (I) wherein a hydroxy, amino, or sulfhydryl group is bonded to any group that, when the prodrug or compound of Formula (I) is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of Formula (I), and the like.

"Stable compound" and "stable structure" are meant to indicate a compound that is sufficiently robust to survive isolation to a useful degree of purity from a reaction mixture, and formulation into an efficacious therapeutic agent.

Synthesis

Throughout the details of the invention, the following abbreviations are used with the following meanings:

Reagents:
MCPBA m-chloroperoxybenzoic acid
DIBAL diisobutyl aluminum hydride
$Et_3N$ triethylamine
TFA trifluoroacetic acid
LAH lithium aluminum hydride
NBS N-bromo succinimide
Red-Al Sodium bis(2-methoxyethoxy)aluminum hydride
$Pd_2 dba_3$ Tris(dibenzylideneacetone)dipalladium(0)
ACE-Cl 2-chloroethylchloroformate Solvents:
THF tetrahydrofuran
MeOH methanol
EtOH ethanol
EtOAc ethyl acetate
HOAc acetic acid
DMF dimethyl formamide
DMSO dimethyl sulfoxide
DME dimethoxyethane
$Et_2O$ diethylether
iPrOH isopropanol Others:
Ar aryl
Ph phenyl
Me methyl
Et ethyl NMR nuclear magnetic resonance
MHz megahertz
BOC tert-butoxycarbonyl
CBZ benzyloxycarbonyl
Bn benzyl
Bu butyl
Pr propyl
cat. catalytic
mL milliliter
nM nanometer
ppm part per million
mmol millimole
mg milligram
g gram
kg kilogram
TLC thin layer chromatography
HPLC high pressure liquid chromatography
rt room temperature
aq. aqueous
sat. saturated The preparation of compounds of Formula (I) of the present invention may be carried out in a convergent or sequential synthetic manner. Detailed synthetic preparations of the compounds of Formula (I) are shown in the following reaction schemes. The skills required in preparation and purification of the compounds of Formula (I) and the intermediates leading to these compounds are known to those in the art. Purification procedures include, but are not limited to, normal or reverse phase chromatography, crystallization, and distillation.

Several methods for the preparation of the compounds of the present invention are illustrated in the schemes and examples shown below. The substitutions are as described and defined above.

Compounds of Formula (I) of this invention may be prepared as shown in Scheme 1. Thus, preparation of an aryl hydrazine (II) is accomplished, for example, by treatment of a corresponding substituted aniline with $NaNO_2$ followed by reduction of the N-nitroso intermediate with a reducing agent such as LAH or zinc and an organic acid, such as acetic acid or trifluoroacetic acid at low temperature. Assembly of the core indole intermediate (IV) is accomplished by Fischer indole cyclization of the aryl hydrazine and a suitably substituted ketone (i.e. (III)) by methods described by, but not limited to, R. J. Sundberg, "Indoles, Best Synthetic Methods" 1996, Academic Press, San Diego, Calif. For example, treatment of the aryl hydrazine (II) as the free base or the corresponding mineral acid salt with the ketone (III) ($R^1$=H, Bn, CBZ, $CO_2Et$, etc) in an alcoholic solvent in the presence of mineral acid affords the indoles (IV) as the free bases (after treatment with aq. NaOH). Reduction of the indoles to the corresponding cis or trans substituted dihydroindoles is accomplished by, for example, treatment with hydrogen in the presence of a catalyst such as platinum oxide or palladium on carbon, or with a metal such as zinc and a mineral acid such as hydrochloric acid, or with sodium and liquid ammonia, or with borane-amine complex such as borane-triethylamine in tetrahydofuran, or preferably by treatment with $NaCNBH_3$ in an acid such as acetic or trifluoroacetic acid or by treatment with a trialkylsilane in nonpolar solvent.

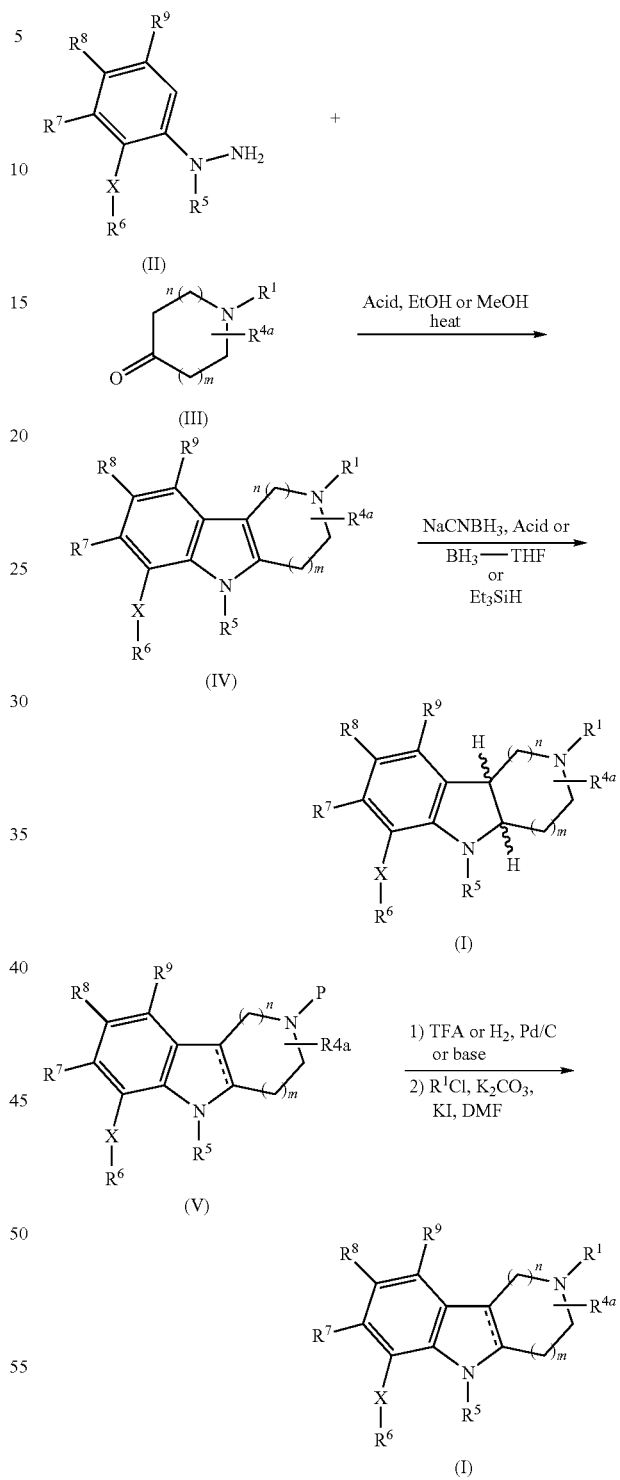

SCHEME I

The corresponding enantiomers can be isolated by separation of the racemic mixture of (I) on a chiral stationary phase column utilizing normal or reverse phase HPLC techniques, the details of which are described in the examples. Alternatively, a diastereomeric mixture of (I) can be prepared by treatment of (I, $R^2$=H) with an appropriate chiral acid (or suitably activated derivative), for example dibenzoyl tartrate or the like (see, for example, Kinbara, K., et. al., *J. Chem. Soc., Perkin Trans.* 2, 1996, 2615; and Tomori, H., et. al., *Bull. Chem. Soc. Jpn.*, 1996, 3581). The diastereomers would then be separated by traditional techniques (i.e. silica chromatography, crystallization, HPLC, etc) followed by removal of the chiral auxiliary to afford enantiomerically pure (I).

In the cases where the carboline nitrogen has been protected (V) (i.e. P=Boc, Bn, CBZ, $CO_2R$), it may be removed under a variety of conditions as described in Greene, T. W., Wuts, P. G. W., "Protective Groups in Organic Synthesis, 2nd Edition", John Wiley and Sons, Inc., New York, pages 309-405, 1991. The free secondary amine could then be alkylated, for example, by treatment with a suitably substituted alkyl halide ($R^1Cl$, or $R^1I$) and a base to afford additional compounds of type (I), as described, for example, by Glennon, R. A., et. al., *Med. Chem. Res.*, 1996, 197.

Compounds of Formula (II) can be prepared as described in Scheme 2. Formation of the aryl amine (VII) may be accomplished by reduction of the corresponding aryl nitro compound (VI). The reduction may be accomplished with a variety of reducing agents, for example, LAH, $SnCl_2$, $NaBH_4$, $N_2H_4$, etc. or with hydrogen in the presence of a suitable catalyst, such as palladium on carbon, or platinum oxide, etc., (see Hudlicky, M., "Reductions in Organic Chemistry", Ellis Horwood, Ltd., Chichester, UK, 1984). Formation of the aryl hydrazine (II) may then be performed as previously described in Scheme 1 or more directly by treatment of the aniline (VII) with aq. hydrochloric acid, stannous chloride and $NaNO_2$ at room temperature (see, Buck, J. S., Ide, W. S., *Org. Syn., Coll. Vol.*, 2, 1943, 130). This latter procedure is especially important when initiating the synthesis with halogenated arylamines (VII). The necessity for preparation of the hydrazine intermediate without the use of strong reductive conditions is critical in these such examples.

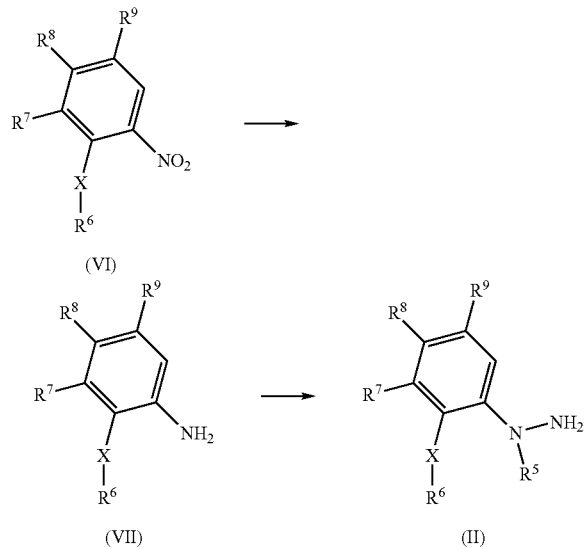

Another related route to hydrazines of Formula (II) is shown in Scheme 3. When an aromatic substitution pattern containing a sulfur or oxygen moiety is desired the following route may be employed. Displacement of a halogen (Cl, F) of a suitably substituted aryl nitro derivative (VIII) by the prerequisite nucleophile under basic conditions affords intermediates of type (IX). Reduction of the nitro moiety followed by elaboration of the resultant amine to the substituted or unsubstituted hydrazine (X) is as described above.

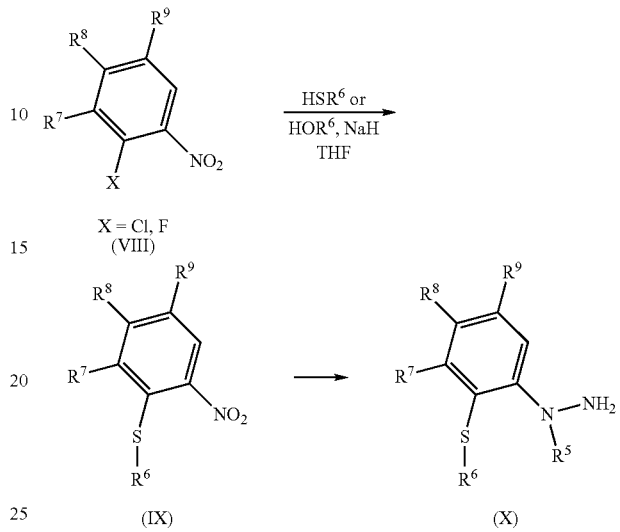

Initiating the synthesis with a nitrobenzene derivative such as (VIII), this approach allows for a variety of derivatization. More highly substituted nitrobenzenes can be obtained by traditional synthetic manipulation (i.e. aromatic substitution) and are known by those in the art (see Larock, R. C., *Comprehensive Organic Transformations*, VCH Publishers, New York, 1989).

Preparation of derivatives of type (I) where X=N is shown in Scheme 4. Fisher indole cyclization of a substituted nitro phenyl hydrazine (XI) with a substituted ketone (III) under previously described conditions affords the tricyclic indoles (XII). Protection of the carboline nitrogen with $Boc_2O$ (if ketone was unsubstituted), followed by selective reduction of the aryl nitro moiety (see Hudlicky, M., *Reductions in Organic Chemistry*, Chapter 8, ACS Monograph 1188, American Chemical Society Pubs., Washington, D.C., 1996). The resultant amine derivatives (XIII) can now be functionalized further, for example, by treatment with an aryl boronic acid under metal catalyzed conditions (see Chan, D. M. T., et.al. *Tetrahedron*, 1998, 39, 2933). Alternatively, the alkylated amine derivatives can be prepared by standard conditions as described by Larock et al. Reduction of the indoles to the cis or trans indolines followed by deprotection, and if desired alkylation of the carboline nitrogen, can be carried out as previously described to afford the desired compounds of type (XV).

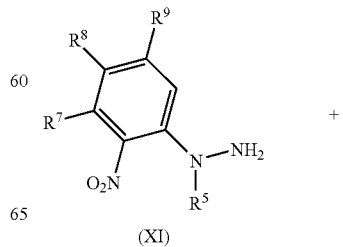

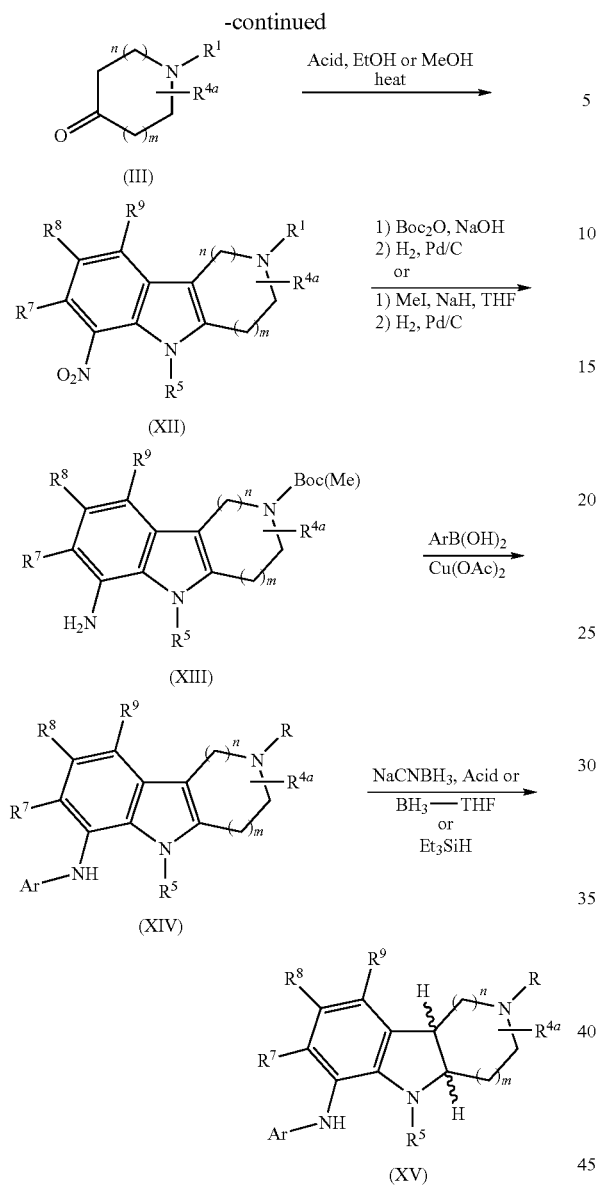
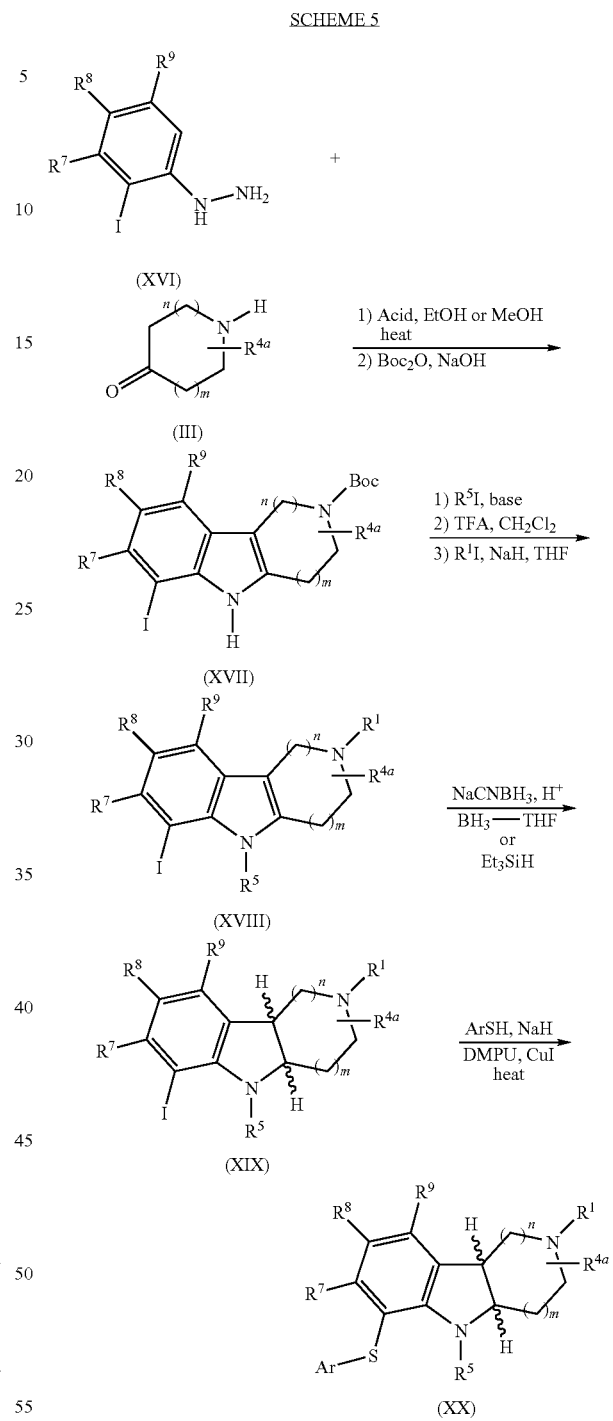

An alternate, more direct approach to differentially substituted analogs is shown in Scheme 5. Initiating the preparation of compounds of type (I) with an aryl iodide expands the versatility of this approach. The preparation of an intermediate which can be functionalized at a later stage is a more efficient approach to some of the substitution types. Fischer indole cyclization of the iodide (XVI) with the ketone (III) as described previously, followed by protection of the amine with Boc$_2$O, affords the iodo indole (XVII). Alkylation of the indole nitrogen under basic conditions followed by removal of the Boc protecting group and a second alkylation of the carboline nitrogen affords the selective differentially substituted carboline indoles (XVIII). Usual reduction of the indole to indoline is carried out without any loss of the aromatic halogen to afford the common aryliodide (XIX). Facile displacement of the iodide with a variety of sulfur nucleophiles under copper catalyzed conditions affords the diaryl iodides (XX).

In addition, there exists a wide range of procedures and protocols for functionalizing haloaromatics, aryldiazonium and aryltriflate compounds. These procedures are well known by those in the art and described, for example, by Stanforth, S. P., *Tetrahedron*, 1998, 263; Buchwald, S. L., et. al., *J. Am. Chem. Soc.*, 1998, 9722; Stille, J. K., et. al., *J. Am. Chem. Soc.*, 1984, 7500. Among these procedures are biaryl couplings, alkylations, acylations, aminations, and amidations. The power of palladium catalyzed functionalization of aromatic cores has been explored in depth in the last decade. An excellent review of this field can be found in J. Tsuji, "Palladium Reagents and Catalysts, Innovations in Organic Synthesis", J. Wiley and Sons, New York, 1995.

One such method to prepare compounds of Formula (I) with substituted $R^1$ sidechains in a more direct manner is shown in Scheme 9. Alkylation of the indole or indoline derivatives (I, $R^1$=H) with a haloalkyl ester, such as $ClCH_2(CH_2)_pCO_2Me$, in the presence of NaI or KI and a base such as $K_2CO_3$, $Na_2CO_3$ or the like, in dioxane or THF or other such solvent while heating (see Glennon, R. A., et. al., *Med. Chem. Res.*, 1996, 197) affords the $R^1$ alkylated esters. Subsequent formation of the activated amides (XXXI) is accomplished by treatment of the ester with N,O-dimethylhydroxylamine hydrochloride and a Lewis acid such as trimethylaluminum or triethylaluminum in toluene (see, for example, Golec, J. M. C., et. al., *Tetrahedron*, 1994, 809) at 0° C. Treatment of the amide (XXX) with a variety of organometallic agents, such as Grignard reagents $R^{1a}MgBr$, alkyl and aryl lithium reagents etc. (see Sibi, M. P., et. al., *Tetrahedron Lett.*, 1992, 1941; and more generally House, H. O., *Modern Synthetic Reactions*, W. A. Benjamin, Inc., Menlo Park, Calif., 1972), in a suitable solvent such as THF, ether, etc. at low temperatures affords the substituted ketones (XXXI).

Furthermore, derivatives of type (I) can be alkylated with any number of functionalized alkyl sidechains. Several examples of these sidechains are described in the experimental section. Typical procedures utilizing standard alkylation of a secondary amine with an alkylhalide under base catalyzed conditions are well known by those skilled in the art.

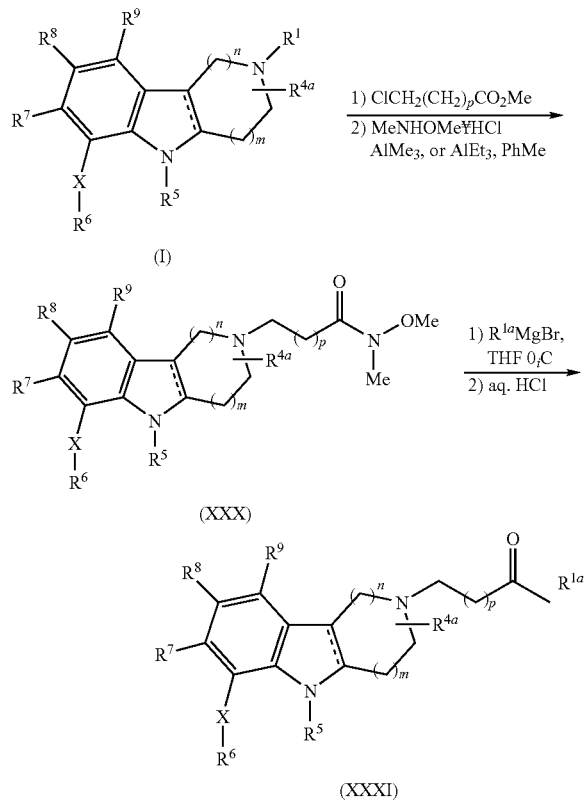

It is understood that for substituents $R^7$, $R^8$, $R^9$, and $R^1$, the compounds of the present invention can be prepared in a number of ways well known to one skilled in the art of organic synthesis. The compounds of the present invention can be synthesized using the methods described herein, together with synthetic methods known in the art of synthetic organic chemistry, or variations thereon as appreciated by those skilled in the art. Additional methods include, but are not limited to, those described in U.S. Pat. Nos. 6,548,493; 6,552,017; and 6,713,471 wherein all three references are hereby incorporated in their entirety by reference.

It is also understood that for substituents $R^1$, $R^{4a}$, $R^{4b}$, $R^5$, $R^6$, $R^7$, $R^8$, $R^9$, n, and X, the compounds of the present invention can be synthesized using the methods described in U.S. Pat. Nos. 6,669,852 and 6,777,406, hereby incorporated in their entirety by reference, together with synthetic methods known in the art of synthetic organic chemistry, or variations thereon as appreciated by those skilled in the art.

EXAMPLES

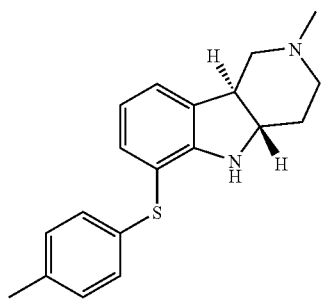

Example 1

Preparation of trans-(4a,9b)-2-methyl-2,3,4,4a,5,9b-hexahydro-1H-pyrido[4,3-b]indol-6-yl-4-methylphenyl sulfide Step A. 2-Tolylsulfanylaniline (2.15 g, 10 mmol) was suspended in conc. HCl (1-3 mL). This mixture was cooled in an ice bath. An aqueous solution (6.5 mL) of $NaNO_2$ (0.7 g, 10 mmol) was added dropwise over 6 min (internal temp <7° C.). The resultant viscous solution was maintained at 0° C. or 2 h at which time it was transferred via cannula to a stirred solution of $SnCl_2$ (3.8 g, 20 mmol) in conc. HCl (4.5 mL) over 10 min. The cooling bath was removed and the reaction mixture was maintained at 0° C. for 20 min and at rt for 1.5 h. Solid product was collected by vacuum filtration, washed with 1N HCl, and dried under vacuum at rt for 18 h to afford 1-{2-[(4-methylphenyl)sulfanyl] phenyl}hydrazine hydrochloride (2.09 g, 78%) as a yellow powder. $^1H$ NMR (300 MHz, $CDCl_3$) δ 7.42 (t, J=8.1 Hz, 2H), 7.10 (s, 4H), 7.03 (t, J=7.3, 2H), 2.26 (s, 3H) ppm.

Step B. 1-{2-[(4-Methylphenyl)sulfanyl]phenyl}hydrazine hydrochloride (1.67 g, 6.27 mmol) and 4-piperidone monohydrate hydrochloride (963 mg, 6.27 mmol) were suspended in 2,2,2-trifluoroethanol (15 mL) at rt. This mixture was heated at 70° C. for 1.5 h, and then allowed to cool to rt. Solid was collected by filtration under vacuum, rinsed with isopropanol, and dried at rt for 18 h to give 4-methylphenyl-2,3,4,5-tetrahydro-1H-pyrido[4,3-b]indol-6-yl sulfide hydrochloride (1.73 g, 84%) as a tan powder. $^1H$ NMR (300 MHz, $CDCl_3$) δ 6.12 (t, J=7.5 Hz, 1H), 5.88 (d, J=7.3 Hz, 1H), 5.71 (t, J=8.1 Hz, 1H), 5.61 (s, 4H), 3.06 (br s, 2H), 2.21 (t, J=6.9 Hz, 1H), 1.74 (t, J=5.8 Hz, 1H) ppm.

Step C. 4-Methylphenyl 2,3,4,5-tetrahydro-1H-pyrido[4,3-b]indol-6-yl sulfide (200 mg, 0.68 mmol) was brought to reflux with formaldehyde (37% aq., 0.68 mL) in MeOH (1.8 mL) for 30 minutes. The reaction was then cooled to 0° C. and sodium borohydride (89 mg, 1.3 mmol) was added slowly. The solution was allowed to stir at room temperature for 2 hours. Ice chips were then added and the reaction partitioned between CHCl₃ and water. The aqueous layer was extracted with CHCl₃ (3×10 mL). The combined extracts were washed with sat. NaCl (10 mL) and dried (MgSO₄) and evaporated. The residue was dissolved in 1 mL EtOH and 1N HCl-Ether was added until no further precipitation was seen. The solid was filtered affording 2-methyl-6-[(4-methylphenyl)sulfanyl]-2,3,4,5-tetrahydro-1H-pyrido[4,3-b]indole as a light tan solid (178 mg, 76%). $^1$H NMR (CD$_3$OD, 300 MHz) δ 7.49 (d, 1H, J=8.1 Hz), 7.26 (d, 1H, J=7.6 Hz), 7.07 (t, 1H, J=7.7 Hz), 6.97-7.02 (m, 4H), 4.42 (s, 2H), 3.58 (t, 2H, J=6.2 Hz), 3.05-3.21 (m, 5H), 2.25 (s, 3H) ppm.

Step D. 2-Methyl-6-[(4-methylphenyl)sulfanyl]-2,3,4,5-tetrahydro-1H-pyrido[4,3-b]indole (77 mg, 0.25 mmol) was dissolved in THF and BH₃-THF (1M, 1.25 mL) was added. The reaction was brought to reflux for 90 minutes. The reaction was then cooled and 6 N HCl (2 mL) was added with acetic acid (0.5 mL). The reaction was brought to reflux again for an additional 30 minutes. The reaction was then cooled and basified to pH 12 with sat. aq. NH₄OH. The aqueous layer was extracted with CHCl₃ (3×10 mL). The combined extracts were washed with sat. NaCl (10 mL), water (10 mL), dried (MgSO₄) and evaporated. The resulting residue was purified by preparatory thin layer chromatography (5% MeOH—CH₂Cl₂). The collected product was dissolved in EtOH (1 mL), and 1N HCl-Ether was added until no further precipitation was seen. The resulting solid was filtered affording the title compound as a light tan solid (45 mg, 52%). $^1$H NMR (CD$_3$OD, 300 MHz) δ 7.09-7.19 (m, 6H), 6.85-6.90 (m, 1H), 4.20-4.23 (m, 1H), 3.62-3.72 (m, 1H), 3.28-3.48 (m, 2H), 3.02-3.21 (m, 2H), 2.97 (s, 3H), 2.30-2.41 (m, 1H), 2.27 (s, 3H), 2.05-2.20 (m, 1H) ppm.

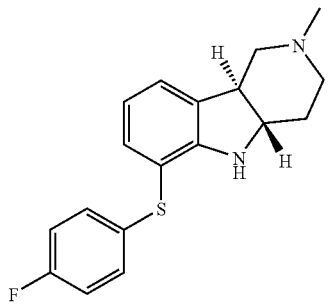

Example 2

Preparation of trans-(4a,9b)-6-[(4-fluorophenyl)sulfanyl]-2-methyl-2,3,4,4a,5,9b-hexahydro-1H-pyrido[4,3-b]indole Step A. To a solution of 4-fluorothiophenol (1.0 g, 7.8 mmol) and 2-chloronitrobenzene (1.2 g, 7.8 mmol) in THF (10 mL) at 0° C. was added NaH (60% dispersion in oil, 390 mg, 9.4 mmol). The reaction was brought to room temperature and allowed to stir for 18 h. Ice was added and the layers separated. The aqueous layer was extracted three times with EtOAc (3×50 mL). The combined extracts were washed with water (50 mL) and dried (Na₂SO₄) and evaporated affording 4-fluorophenyl 2-nitrophenyl sulfide (1.6 g, 82%) as a yellow solid. $^1$H NMR (CDCl$_3$, 300 MHz) δ 8.24 (dd, 1H, J=1.5, 8 Hz), 7.58-7.63 (m, 2H), 7.38 (dt, 1H, J=1.5, 7.4 Hz), 7.15-7.25 (m, 3H), 6.82 (dd, $^1$H, J=1.1, 8.1 Hz) ppm.

Step B. 4-Fluorophenyl-2-nitrophenyl sulfide (1.6 g, 6.4 mmol) was combined with palladium hydroxide (200 mg) in EtOH (100 mL) and stirred for 18 hours under H₂ (55 psi). The mixture was filtered through Celite and the filtrate concentrated to give a dark solid. The residue was taken up in a minimal amount of EtOAc (15 mL) and 1N HCl/Ether was added until precipitation was no longer seen to occur. The solid was filtered, washed with EtOAc (30 mL) and dried affording 2-[(4fluorophenyl)sulfanyl]aniline hydrochloride in 40% yield (0.65 g). $^1$H NMR (CD$_3$OD, 300 MHz) δ 7.22-7.41 (m, 6H), 7.02-7.12 (m, 2H) ppm.

Step C. 2-[(4-Fluorophenyl)sulfanyl]aniline (400 mg, 1.6 mmol) was stirred at 0° C. in conc. HCl (4.0 mL) and NaNO₂ (130 mg, 1.8 mmol) was added slowly, maintaining 0° C. reaction temperature. After stirring for 1 hour at 0° C., a solution of SnCl₂ (610 mg, 3.2 mmol) in 1.5 mL conc. HCl was added. The reaction was brought to rt and stirred for one h. Upon completion, the reaction was basified with 1N aqueous NaOH to pH 12. The reaction mixture was partition between water and CHCl₃ and the aqueous layer extracted with CHCl₃ (3×20 mL). The combined extracts were washed with brine (20 mL), H₂O (20 mL) and dried (Na₂SO₄) and evaporated to a residue. The residue was taken up in a minimal amount of CHCl₃ (10 mL) and 1N HCl-Ether (10 mL) was added. The solvent was evaporated affording 1-{2-[(4-fluorophenyl)sulfanyl]phenyl}hydrazine hydrochloride as a dark semi-solid (327 mg, 76%). $^1$H NMR (CD$_3$OD, 300 MHz) δ 7.40-7.51 (m, 2H), 7.16-7.25 (m, 2H), 6.95-7.14 (m, 4H) ppm.

Step D. 1-{2-[(4-Fluorophenyl)sulfanyl]phenyl}hydrazine (110 mg, 0.40 mmol) and monohydrate piperidone hydrochloride (160 mg, 0.41 mmol) were dissolved in trifluoroethanol (1 mL) and brought to 80° C. for two hours. The solid, which had precipitated, was filtered, rinsed with isopropanol (10 mL) and dried to give 4-fluorophenyl-2,3,4,5-tetrahydro-1H-pyrido[4,3-b]indol-6-yl sulfide hydrochloride in 94 mg (77%). $^1$H NMR (CD$_3$OD, 300 MHz) δ 7.51 (d, 1H, J=7.7 Hz), 7.29 (d, 1H, J=7.3 Hz), 7.12 (m, 3H), 6.93 (t, 2H, J=8.8 Hz), 4.43 (s, 2H), 3.58 (t, 2H, J=6.3 Hz), 3.11 (t, 2H, 6.3 Hz) ppm. MS (CI, NH₃) 299, (M+H).

The Title compound was prepared using the procedure of Example 1 Step C and D. The compound was purified by preparative TLC (6% MeOH/CH₂Cl₂). The collected compound was then dissolved in a minimal amount of ether and 1N HCl-Ether was added until no further precipitation was seen. The solid was filtered affording the title compound as a light tan solid (83%). $^1$H NMR (CD$_3$OD, 300 MHz) δ 7.05-7.20 (m, 4H), 6.97 (t, 2H, J=6.6 Hz), 6.72 (d, 1H, J=7.3 Hz), 3.49 (dd, 1H, J=3.3, 10.6 Hz), 2.95-3.03 (m, 2H), 2.79-2.89 (m, 1H), 2.38 (s, 3H), 2.10-2.25 (m, 2H), 2.01-2.10 (m, 1H), 1.78-1.95 (m, 1H) ppm.

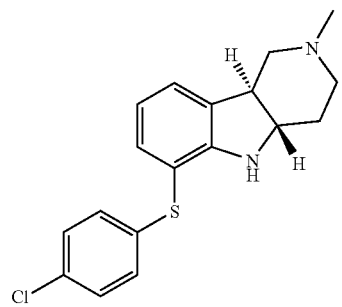

Example 3

Preparation of trans-(4a,9b)-6-[(4-chlorophenyl)sulfanyl]-2-methyl-2,3,4,4a,5,9b-hexahydro-1H-pyrido [4,3-b]indole Step A. The following compound was prepared in 89% yield by substituting the required thiophenol for 4-chlorothiophenol by the procedure in Example 2, Step A. $^1$H NMR (CDCl$_3$, 300 MHz): δ 8.23 (dd, 1H, J=1.4, 8 Hz), 7.23-7.48 (m, 4H), 7.36 (dt, 1H, J=1.4, 7.3 Hz), 7.20-7.29 (m, 1H), 6.86 (dd, 1H, J=1.1, 8.1 Hz) ppm.

Step B. The following compound was prepared in 80% yield by the procedure of Example 2, Step B. $^1$H NMR (CD$_3$OD, 300 MHz) δ 7.41-7.58 (m, 4H), 7.35 (d, 2H, J=8.4 Hz), 7.23 (d, 2H, J=8.7 Hz) ppm.

Step C. The following compound was prepared in 94% yield according to the procedure for Example 2, Step C. $^1$H NMR (CD$_3$OD, 300 MHz) δ 7.42-7.55 (m, 2H), 7.25 (d, 2H, J=8.4 Hz), 7.07 (d, 2H, J=8.87 Hz), 7.02-7.10 (m, 2H) ppm.

Step D. The title compound was prepared by the method of Example 2, step D in 78% yield. $^1$H NMR (CD$_3$OD, 300 MHz) δ 7.55 (d, 1H, J=8.1 Hz), 7.38 (d, 1H, J=8.0 Hz), 7.12-7.18 (m, 3H), 6.96 (d, 2H, J=8.8 Hz), 4.41 (s, 2H), 3.52-3.59 (m, 2H), 3.03-3.11 (m, 2H) ppm.

Step E. 2-Methyl-6-[(4-chlorophenyl)sulfanyl]-2,3,4,5-tetrahydro-1H-pyrido[4,3-b]indole (24 mg, 0.08 mmol) in THF (0.5 mL) was stirred at room temperature under N$_2$. BH$_3$-THF (0.40 mmol, 1M) was added dropwise and the reaction was brought to reflux for 90 minutes. The reaction was cooled to room temperature, 6 N HCl (0.5 mL) was added and the reaction was brought to reflux for an additional 90 minutes. The mixture was cooled to 0° C. and basified to a pH of 12 with 50% NaOH. The aqueous mixture was extracted with CHCl$_3$ (3×10 mL). The combined extracts were washed with brine (10 mL), H$_2$O (10 mL), dried (Na$_2$SO$_4$) and evaporated leaving a yellow residue. Purification was accomplished by prep TLC (6% MeOH—CH$_2$Cl$_2$). The collected residue was dissolved in EtOAc (0.5 mL), and fumaric acid (4.6 mg, 0.04 mmol) in MeOH (0.5 mL) was added. The solution was stirred for 10 minutes. The solvent was evaporated and the resulting solid was recrystallized in isopropylalcohol affording the title compound as a light tan solid (20 mg, 83%). $^1$H NMR (CD$_3$OD, 300 MHz) δ 7.15-7.23 (m, 4H), 7.04 (d, 2H, J=8.8 Hz), 6.79 (t, 1H, J=7.7 Hz), 6.67 (s, 2H), 4.12-4.19 (m, 1H), 3.55-3.63 (m, 2H), 3.31-3.40 (m, 1H), 3.19-3.22 (m, 1H), 2.98-3.10 (m, 2H), 2.91 (s, 3H), 2.20-2.29 (m, 1H), 2.01-2.12 (m, 1H) ppm.

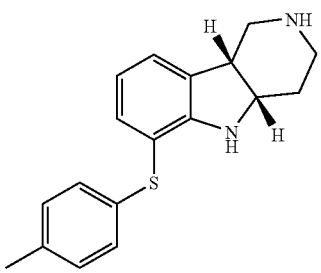

Example 4

Preparation of cis-6-[(4-methylphenyl)sulfanyl]-2,3,4,4a,5,9b-hexahydro-1H-pyrido[4,3-b]indole (2E)-2-butenedioic acid 4-Methylphenyl 2,3,4,5-tetrahydro-1H-pyrido[4,3-b]indol-6-yl sulfide hydrochloride (prepared in Example 1, 331 mg, 1.0 mmol) was suspended in TFA (17 mL) at rt. This mixture was cooled in an ice bath. A stream of N$_2$ was introduced through the solution while solid NaCNBH$_3$ (202 mg, 3.3 mmol) was added in 4 portions over 10 min. maintaining an internal temperature of <7° C. The resultant solution was maintained at ~0° C. for 5 h at which time it was poured onto ice chips. With vigorous stirring, 50% NaOH was added portionwise to pH 12. This mixture was extracted with CHCl$_3$ (3×100 mL). The organic extracts were combined, dried (MgSO$_4$) and concentrated in vacuo. The residue (265 mg, 90%) was treated with Et$_2$O (5 mL) and filtered. The filtrate was treated with a MeOH solution (1 mL) of fumaric acid (116 mg, 1.0 mmol). The resultant solution was concentrated in vacuo. The solid residue was recrystallized from EtOAc-Et$_2$O to afford the title compound (298 mg, 67%) as a crystalline sample. $^1$H NMR (300 MHz, CDCl$_3$) δ 7.18 (d, J=7.7 Hz, 1H), 7.09 (d, J=7.0 Hz, 1H), 7.29 (s, 4H), 6.72 (t, J=7.3 Hz, 1H), 4.09 (t, J=8.3 Hz, 1H), 3.83 (q, J=5.5 Hz, 1H), 3.2-2.8 (m, 3H), 2.72-2.60 (m, 1H), 2.28 (s, 3H), 1.78-1.63 (m, 2H), 1.57-1.44 (m, 2H) ppm.

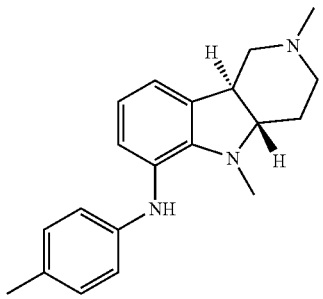

Example 5

Preparation of trans-(4a,9b)-2,5-dimethyl-N-(4-methylphenyl)-2,3,4,4a,5,9b-hexahydro-1H-pyrido [4,3-b]indol-6-amine Preparation of Step A. 2-Nitrophenylhydrazine (3.7 g, 24.2 mmol) and 4-piperidone monohydrate hydrochloride (3.7 g, 24.2 mmol) were suspended in 2,2,2-trifluoroethanol (25 mL). The resultant mixture was heated at reflux for 2 h and then concentrated. Conc. HCl (35 mL) was added in one portion. The resultant mixture was then heated at 105° C. for 15 h, and allowed to cool to rt, after which it was poured onto ice. While vigorously stirring, a 50% NaOH solution was added portionwise over 10 min until pH 12, maintaining the internal temperature at <20° C. The solid was collected via filtration and dried at room temperature under vacuum for 18 h to afford 6-nitro-2,3,4,5-tetrahydro-1H-pyrido[4,3-b]indole (2.91 g, 55%). $^1$H NMR (300 MHz, DMSO) δ 11.65-11.60 (br s, 1H), 7.96 (d, J=8.1 Hz, 1H), 7.80 (d, J=7.0 Hz, 1H), 7.12 (t, J=8.0 Hz, 1H), 3.86 (s, 2H), 2.99 (br s, 2H), 2.72 (br s, 2H) ppm.

Step B. 6-Nitro-2,3,4,5-tetrahydro-1H-pyrido[4,3-b]indole (250 mg, 0.99 mmol) was dissolved in CH$_2$Cl$_2$ (2.5 mL) with sat. aq. K$_2$CO$_3$. Ethylchloroformate (130 mg, 1.2 mmol) was added at 0° C. The reaction was brought to room temperature and stirred for 15 h. The layers were separated and the aqueous layer was extracted with CHCl₃ (3×5 mL). The combined extracts were washed with brine (10 mL), dried (MgSO₄) and evaporated affording ethyl-6-nitro-1,3,4,5-tetrahydro-2H-pyrido[4,3-b]indole-2-carboxylate as an orange semi-solid (160 mg, 56%). ¹H NMR (CDCl₃, 300 MHz) δ 8.17 (d, 1H, J=8.1 Hz), 7.78 (d, 1H, J=7.6 Hz), 3.19 (t, 1H, J=8.1 Hz), 4.73 (s, 2H), 4.18-4.23 (m, 4H), 2.91-2.98 (m, 2H), 1.30-1.39 (t, 3H, J=6.9 Hz) ppm.

Step C. Ethyl 6-nitro-1,3,4,5-tetrahydro-2H-pyrido[4,3-b]indole-2-carboxylate (0.33 g, 1.12 mmol) was combined with KOH (0.31 g, 5.6 mmol) and iodomethane (1.3 g, 8.96 mmol) in ethylene glycol dimethyl ether (5.6 mL) and stirred at 90° C. for 16 h. The inorganic solid was filtered and the filtrate evaporated to give ethyl-5-methyl-6-nitro-1,3,4,5-tetrahydro-2H-pyrido[4,3-b]indole-2-carboxylate (0.37 g) as an orange oil in near quantitative yield. ¹H NMR (CDCl₃, 300 MHz) δ 7.74 (d, 1H, J=7.7 Hz), 7.67 (d, 1H, J=7.7 Hz), 7.12 (t, 1H, J=8.0 Hz), 4.70 (s, 2H), 4.22 (q, 2H, J=7.0 Hz), 3.91 (br. s, 2H), 3.62 (s, 3H), 2.84 (t, 2H, J=5.5 Hz), 1.30 (t, 3H, J=7.0 Hz) ppm.

Step D. Ethyl 5-methyl-6-nitro-1,3,4,5-tetrahydro-2H-pyrido[4,3-b]indole-2-carboxylate (340 mg, 1.12 mmol) and palladium hydroxide (60 mg) were dissolved in EtOH (50 mL) and stirred for 18 h under H₂ (55 psi). The mixture was filtered through Celite and the filtrate was evaporated to give ethyl 6-amino-5-methyl-1,3,4,5-tetrahydro-2H-pyrido[4,3-b]indole-2-carboxylate as a light tan solid (202 mg, 66%). ¹H NMR (CDCl₃, 300 MH) δ 6.85-7.02 (m, 2H), 6.43-6.51 (d, 1H, J=7.0 Hz), 4.80 (br. s, 2H), 4.21 (q, 2H, J=6.6 Hz), 3.90 (s, 3H), 3.80-3.88 (m, 2H), 2.75-2.80 (m, 2H), 1.27 (t, 3H, J=7.3 Hz) ppm.

Step E. Ethyl 6-amino-5-methyl-1,3,4,5-tetrahydro-2H-pyrido[4,3-b]indole-2-carboxylate (103 mg, 0.37 mmol) was combined with p-tolylboronic acid (100 mg, 0.74 mmol), triethylamine (75 mg, 0.74 mmol), and copper (II) acetate (68 mg, 0.37 mmol) in CH₂Cl₂ (2 mL) and allowed to stir for 36 h. The solvent was evaporated and the residue purified by silica gel column chromatography (20% EtOAc-Hex) affording ethyl 5-methyl-6-(4-toluidino)-1,3,4,5-tetrahydro-2H-pyrido[4,3-b]indole-2-carboxylate as a green semi-solid (73 mg, 73%) yield. ¹H NMR (CDCl₃, 300 MHz) δ 7.32 (d, 1H, J=7.7 Hz), 7.03 (t, 1H, J=7.7 Hz), 6.97 (d, 2H, J=8.0 Hz), 6.92 (d, 1H, J=6.9 Hz), 6.54 (d, 2H, J=8.4 Hz), 5.37 (s, 1H), 4.70 (s, 2H), 4.21 (q, 2H, J=7.0 Hz), 3.88 (br. s, 2H), 3.71 (s, 3H), 2.76 (t, 2H, J=5.5 Hz), 2.24 (s, 3H), 1.30 (t, 3H, J=7.3 Hz) ppm.

Step F. Ethyl-5-methyl-6-(4-toluidino)-1,3,4,5-tetrahydro-2H-pyrido[4,3-b]indole-2-carboxylate (73 mg, 0.214 mmol) was dissolved in anhydrous THF (1 mL) under N₂ and LAH (1M in THF, 0.42 mmol) was added slowly. The reaction was brought to reflux for 2 hours. The reaction was quenched by the addition of water (16 μL), 15% aq. NaOH (16 μL) and then water (49 μL). The reaction was allowed to stir for 10 minutes between each addition. The aluminum salts were removed by filtration. The filtrate was evaporated and purified by silica gel column chromatography (10%, then 20% EtOAc-Hex) to give 2,5-dimethyl-N-(4-methylphenyl)-2,3,4,5-tetrahydro-1H-pyrido[4,3-b]indol-6-amine (15 mg, 23%). ¹H NMR (CDCl₃, 300 MH₂) δ 7.23-7.27 (m, 1H), 6.89-7.03 (m, 3H), 6.88 (d, 1H, J=7.3 Hz), 6.54 (d, 2H, J=8.4 Hz), 3.70 (s, 5H), 2.79-2.89 (m, 4H), 2.58 (s, 3H), 2.23 (s, 3H) ppm.

Step G. 2,5-Dimethyl-N-(4-methylphenyl)-2,3,4,5-tetrahydro-1H-pyrido[4,3-b]indol-6-amine (0.047 g, 0.162 mmol) was dissolved in THF (1 mL) and BH₃-THF (1 M, 0.810 mL) and brought to reflux under N₂ for 15 hours. The solvent was evaporated and 6N HCl (2 mL) and the reaction brought to 80° C. for an additional 2 hours. The reaction was then basified to a pH of 12 with 50% aq. NaOH. The aqueous mixture was then extracted with CHCl₃ (3×20 mL). The combined extracts were washed with brine (10 mL), dried (MgSO₄) and evaporated leaving a light tan residue. Purification was accomplished by silica gel column chromatography (2.5% MeOH/CH₂Cl₂) followed by chiral separation by HPLC (Chiralcel OD, 10% EtOH-Hex, 7 mL/min) affording the title compound. Total yield of both enantiomers was 53%. ¹H NMR (CDCl₃, 300 MHz) δ 6.92-7.03 (m, 3H), 6.86 (d, 1H, J=7.3 Hz), 6.77 (t, 1H, J=7.7 Hz), 6.65 (d, 2H, J=8.4 Hz), 5.11 (s br, 1H), 3.49 (dd, 1H, J=2.5, 10.2 Hz), 3.10 (d, 1H, J=11.7 Hz), 2.81-2.91 (m, 1H), 2.77 (s, 3H), 2.44 (s, 3H), 2.26 (s, 3H), 2.00-2.23 (m, 3H), 1.81-1.92 (m, 2H) ppm.

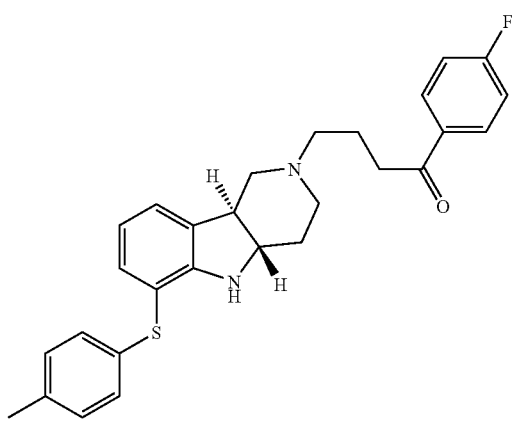

Example 6

Preparation of trans-4-{(4a,9b)-6-[(4-methylphenyl)sulfanyl]-1,3,4,4a,5,9b-hexahydro-2H-pyrido[4,3-b]indol-2-yl}-1-(4-fluorophenyl)-1-butanone Trans(4a,9b)-6-[(4-methylphenyl)sulfanyl]-2,3,4,4a,5,9b-hexahydro-1H-pyrido[4,3-b]indole (50 mg, 0.17 mmol) was combined with 4-chloro-1-(4-fluorophenyl)-1-butanone (41 mg, 0.20 mmol), potassium carbonate (93 mg, 0.67 mmol) and potassium iodide (28 mg, 0.17 mmol) in methyl ethyl ketone (1 mL) and allowed to reflux for 48 hours. The inorganics were filtered and the filtrate evaporated to afford a residue. Purification of the residue was accomplished by silica gel column chromatography (50% EtOAc/Hex) to afford the title compound as a light yellow oil (43 mg, 56%). ¹H NMR (CDCl₃, 300 MHz) δ 7.98 (q, 2H, J=5.1 Hz), 7.05-7.19 (m, 2H), 7.02 (s, 4H), 6.69 (t, 1H, J=7.6 Hz), 4.04 (s, 1H), 3.71-3.76 (m, 1H), 3.15-3.22 (m, 1H), 2.97 (t, 2H, J=7.3 Hz), 2.62-2.71 (m, 1H), 2.32-2.43 (m, 4H), 2.28 (s, 3H), 1.95 (t, 2H, J=7.3 Hz), 1.58-1.80 (m, 3H) ppm.

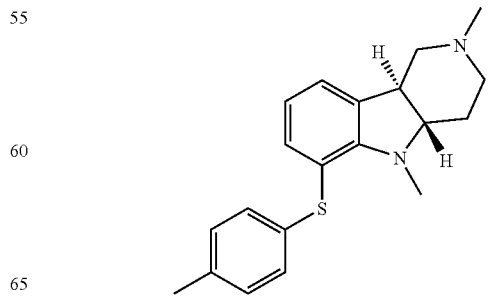

Example 7

Preparation of (4aS,9bR)-2,5-dimethyl-6-[(4-methylphenyl)sulfanyl]-2,3,4,4a,5,9b-hexahydro-1H-pyrido[4,3-b]indole Step A. 2-Iodoaniline (16 g, 73 mmol) was suspended in concentrated hydrochloric acid (100 mL), and then cooled to 0° C. in an ice bath. Sodium nitrite (6 g, 87.6 mmol) in water (25 mL) was added slowly to reaction mixture and then reaction allowed to stir at 0° C. for 1.5 hours. In a separate flask, tin (II) chloride (84.7 g, 182.5 mmol) was dissolved in concentrated hydrochloric acid (12 mL) and added slowly over 30 minutes to reaction mixture. The resulting suspension was allowed to warm to room temperature and stirred for 14 h. The solid was filtered off, and allowed to dry to afford 1-(2-iodophenyl)hydrazine hydrochloride (19 g, 96%). $^1$H NMR (CDCl$_3$, 300 MHz) δ 7.82 (dd, 1H, J=1.1, 7.7 Hz), 7.39 (dt, 1H, 1.2, 7.7 Hz), 6.96 (dd, 1H, J=1.1, 8.1 Hz), 6.82 (dt, 1H, J=1.1, 7.5) ppm. MS (ApCI) 275 (M$^+$+CH$_3$CN+H).

Step B. 1-(2-iodophenyl)hydrazine hydrochloride (1.67 g, 6.2 mmol) and 4-piperidone monohydrate hydrochloride (0.952 g, 6.2 mmol) were dissolved in trifluoroethanol (15 mL) and concentrated hydrochloric acid (5 mL) and heated at 87° C. and solid was filtered, washed with cold isopropyl alcohol (50 mL), and dried to give 6-iodo-2,3,4,5-tetrahydro-1H-pyrido[4,3-b]indole hydrochloride (1.76 g, 85%) as a tan solid. $^1$H NMR (CD$_3$OD, 300 MHz) δ 7.49 (d, 1H, J=7.7 Hz), 7.43 (d, 1H, J=8 Hz), 6.82 (t, 1H, J=7.7 Hz), 4.40 (s, 2H), 3.60 (t, 2H, J=6.25 Hz), 3.18 (t, 2H, J=5.85 Hz) ppm.

Step C. 6-Iodo-2,3,4,5-tetrahydro-1H-pyrido[4,3-b]indole hydrochloride (7 g, 21 mmol) was suspended in CH$_2$Cl$_2$ (150 mL) and to this suspension was added 4-(dimethyl amino)pyridine (0.1 g, 0.82 mmol) and saturated potassium carbonate solution (150 mL) with stirring. Then di-tertbutyl dicarbonate (5.5 g, 25.2 mmol) in dichloromethane (20 mL) was added in 5 portions over 5 minutes. The resulting two-phase mixture was stirred vigorously at room temperature for 1.5 h. Layers were separated and aqueous layer was back extracted with CH$_2$Cl$_2$ (2×100 mL). The organics were collected, dried over magnesium sulfate, filtered and then concentrated under reduced pressure to give tert-butyl 6-iodo-1,3,4,5-tetrahydro-2H-pyrido[4,3-b]indole-2-carboxylate (7.06 g, 84%). $^1$H NMR (CDCl$_3$ 300 MHz) δ 7.63 (d, 1H, J=7.7 Hz), 7.38 (d, 1H, J=7.7 Hz), 6.76 (t, 1H, J=7.5 Hz), 4.59 (br s, 2H), 3.82 (br s, 2H), 2.78 (t, 2H, J=5.3 Hz), 1.49 (s, 9H) ppm.

Step D. Tert-butyl 6-iodo-1,3,4,5-tetrahydro-2H-pyrido[4,3-b]indole-2-carboxylate (6.8 g, 17 mmol) was dissolved in DME (50 mL), and potassium hydroxide (4.8 g, 85.4 mmol) and iodomethane (15.7 g, 110.5 mmol) were added and heated at 80° C. in a pressure vessel for 3 h. The reaction was cooled to room temperature and diluted with ethyl acetate (50 mL). The solids were removed by vacuum filtration. The filtrate was concentrated under reduced pressure to give a brown oil (5.5 g, 79% crude yield). The oil was dissolved in CH$_2$Cl$_2$ (30 mL). Trifluoroacetic acid (30 mL) was added in ten portions over 5 minutes and stirred for 30 minutes. The reaction was basified with 50% sodium hydroxide to pH 10. This mixture was extracted with CH$_2$Cl$_2$ (3×150 mL). The organics were collected, dried over magnesium sulfate, filtered and then concentrated under reduced pressure to give 6-iodo-5-methyl-2,3,4,5-tetrahydro-1H-pyrido[4,3-b]indole (3.85 g, 73%). $^1$H NMR (CDCl$_3$ 300 MHz) δ 7.62 (d, 1H, J=7.6 Hz), 7.33 (d, 1H, J=7.7 Hz), 6.74 (t, 1H, J=7.5 Hz), 4.03 (s, 2H), 3.95 (s, 3H), 3.26 (t, 2H, J=5.6 Hz), 2.71 (t, 2H, J=5.6 Hz) ppm.

Step E. 6-Iodo-5-methyl-2,3,4,5-tetrahydro-1H-pyrido[4,3-b]indole (3.85 g, 12.3 mmol) was suspended in methanol (40 mL). Formaldehyde (14 mL of 37%) was added and heated at reflux for 2 h. The reaction was cooled to 0° C. in an ice bath and sodium borohydride (1.7 g, 46 mmol) was added slowly over 15 minutes and stirred for two h at 0-10° C. The reaction was diluted with water (200 mL) and extracted with CH$_2$Cl$_2$ (3×150 mL). The organics were collected, washed with brine (250 mL), dried over magnesium sulfate, filtered and concentrated under reduced pressure. The product was purified by silica gel column chromatography (3% MeOH/CH$_2$Cl$_2$) to give 6-iodo-2,5-dimethyl-2,3,4,5-tetrahydro-1H-pyrido[4,3-b]indole (0.6 g, 15%). $^1$H NMR (CDCl$_3$ 300 MHz) δ 7.59 (d, 1H, J=7.4 Hz), 7.33 (d, 1H, J=7.6 Hz), 6.73 (t, 1H, J=7.7 Hz), 3.98 (s, 3H), 3.62 (s, 2H), 2.83 (s, 4H), 2.55 (s, 3H) ppm.

Step F. 6-Iodo-2,5-dimethyl-2,3,4,5-tetrahydro-1H-pyrido[4,3-b]indole (1 g, 3 mmol) was dissolved in BH$_3$-THF complex (15 mL) and heated at 75° C. for 18 h in a pressure vessel. The reaction was cooled to room temperature and concentrated under reduced pressure to a residue. The residue was heated at reflux in 6N hydrochloric acid (15 mL) for 3.5 h. The reaction was basified with 50% sodium hydroxide to pH 10. The mixture was extracted with CH$_2$Cl$_2$ (3×100 mL). The organics were collected, dried over magnesium sulfate, filtered and concentrated under reduced pressure. The residue was purified by silica gel column chromatography (4% methanol, dichloromethane) to give trans(4a,9b)-6-iodo-2,5-dimethyl-2,3,4,4a,5,9b-hexahydro-1H-pyrido[4,3-b]indole (0.12 g, 12%). $^1$H NMR (CDCl$_3$ 300 MHz) δ 7.56 (dt, 1H, J=2.2, 8.1 Hz), 7.33 (d, 1H, J=7.3 Hz), 6.50 (t, 1H, J=7.5 Hz), 3.48-3.41 (m, 1H), 3.04 (s, 3H), 2.86-2.75 (m, 1H), 2.42 (s, 3H), 2.20-2.13 (m, 3H), 1.93-1.78 (m, 1H) ppm.

Step G. (4aS,9bR)-6-Iodo-2,5-dimethyl-2,3,4,4a,5,9b-hexahydro-1H-pyrido[4,3-b]indole (910 mg, 2.7 mmol) was combined with p-tolylthiophenol (426 mg, 3.3 mmol), sodium hydride (132 mg, 3.3 mmol, 60% in oil dispersion), copper iodide (515 mg, 2.7 mmol) and 1,3-dimethyl-3,4,5,6-tetrahydro-2(1H)-pyrimidinone (5 mL) and stirred at 100° C. for 16 hours. The reaction mixture was partitioned between water and CHCl$_3$. The aqueous layer was extracted with CHCl$_3$ (3×20 mL). The combined organics were washed with sat. NaCl (10 mL), water (10 mL), dried (MgSO$_4$) and evaporated. The residue was loaded onto a SCX resin. The resin was washed with 150 mL of MeOH followed by washing with 2.0 M methanolic ammonia. The collected residue was dissolved in CH$_3$CN and $^1$N HCl/Ether was added until no further precipitation was observed. The solid was filtered and washed with CH$_3$CN affording the title compound (315 mg, 36%) as a white solid. $^1$H NMR (CD$_3$OD, 300 MHz) δ 7.20 (d, 1H, J=7.7 Hz), 7.14 (d, 1H, J=7.3 Hz), 7.06 (d, 2H, J=8.1 Hz), 6.97 (d, 2H, J=8.4 Hz), 6.82-6.87 (m, 1H), 3.99-4.05 (m, 1H), 3.71-3.80 (m, 1H), 3.15-3.25 (m, 4H), 3.08 (s, 3H), 2.99 (s, 3H), 2.38-2.43 (m, 1H), 2.26 (s, 3H), 1.90-2.03 (m, 1H) ppm.

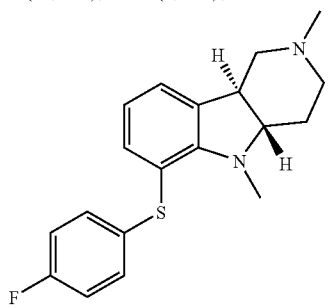

Example 8

Preparation of trans(4a,9b)-6-[(4-fluorophenyl)sulfanyl]-2,5-dimethyl-2,3,4,4a,5,9b-hexahydro-1H-pyrido[4,3-b]indole 4-Fluorobenzenethiol (0.015 g, 0.12 mmol), copper iodide (0.022 g, 0.12 mmol) and sodium hydride (0.005 g, 0.12 mmol) were dissolved in 1,3-dimethyl-3,4,5,6-tetrahydro-2 (1H)-pyrimidinone (0.75 mL), and heated to 40° C., and Trans(4a,9b)-6-iodo-2,5-dimethyl-2,3,4,4a,5,9b-hexahydro-1H-pyrido[4,3-b]indole (0.032 g, 0.097 mmol) in 1,3-dimethyl-3,4,5,6-tetrahydro-2(1H)-pyrimidinone (0.50 mL) was added. This mixture was heated to at 100° C. for 48 h. The reaction was cooled to room temperature and diluted with water (5 mL) and chloroform (5 mL). The organics were separated, dried over magnesium sulfate, filtered, and concentrated under reduced pressure to an oil. The oil was purified by silica gel column chromatography, (3% methanol/chloroform), followed by HPLC purification on a ChiralCel OD column (2.5% isopropyl alcohol, hexanes) to afford the title compound as an oil (10 mg, 6.8%). $^1$H NMR (CDCl$_3$, 300 MHz) δ 7.15-7.1 (m., 3H), 7.09-6.89 (m, 3H), 6.73 (t, 1H, J=7.5), 3.44 (d, 1H, J=10.6), 3.09 (s br, 1H), 3.05 (s, 3H), 2.82 (t, 1H, J=11.9), 2.52-2.46 (m, 1H), 2.42 (s, 3H), 2.22-2.02 (m, 4H), 1.87-1.79 (m, 1H) ppm.

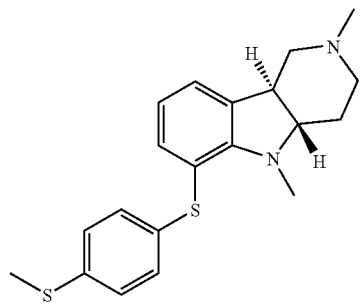

Example 9

Preparation of trans(4a,9b)-2,5-dimethyl-6-{[4-(methylsulfanyl)phenyl]sulfanyl}-2,3,4,4a,5,9b-hexahydro-1H-pyrido[4,3-b]indole Step A. 4-Thiomethylphenylthiol (0.049 g, 0.31 mmol), copper iodide (0.059 g, 0.31 mmol) and sodium hydride (0.062 g, 0.26 mmol) were dissolved in 1,3-dimethyl-3,4,5,6-tetrahydro-2(1H)-pyrimidinone (1 mL), and heated to 40° C. Ethyl 6-iodo-5-methyl-1,3,4,5-tetrahydro-2H-pyrido[4,3-b]indole-2-carboxylate (100 mg, 0.26 mmol) in 1,3-dimethyl-3,4,5,6-tetrahydro-2(1H)-pyrimidinone (1 mL) was added. The mixture was heated to at 90° C. for 48 h. The reaction was cooled to room temperature, diluted with water (5 mL) and chloroform (5 mL), and the organics were separated. The organic layer was washed with brine (10 mL), water (10 mL), dried over magnesium sulfate, filtered and concentrated under reduced pressure to give an oil. The oil was purified by silica gel column chromatography, (3% methanol, chloroform) to afford Ethyl 5-methyl-6-{[4-(methylsulfanyl)phenyl]sulfanyl}-1,3,4,5-tetrahydro-2H-pyrido [4,3-b]indole-2-carboxylate as an oil. $^1$H NMR (CDCl$_3$, 300 MHz) δ 7.51 (d, 1H, J=7.6 Hz), 7.33 (d, 1H, J=7.3 Hz), 7.11-7.05 (m, 3H), 6.93 (d, 2H, J=8.4 Hz), 4.69 (s, 2H), 4.20 (q, 2H, J=7.06 Hz), 3.89 (s, 5H), 2.76 (t, 2H, J=5.2), 2.41 (s, 3H), 1.32-1.25 (m, 3H) ppm.

Step B. To a dry THF solution (2 mL) of ethyl-5-methyl-6-{[4-(methylsulfanyl)phenyl] sulfanyl}-1,3,4,5-tetrahydro-2H-pyrido[4,3-b]indole-2-carboxylate (0.17 g, 0.41 mmol) was added dropwise over 15 min a THF solution of lithium aluminum hydride (1 mL, 1M in THF) at 0° C. The reaction was stirred at room temperature for 1 h. The reaction was quenched with water (0.04 mL) and stirred for 110 minutes. A 15% sodium hydroxide solution (0.04 mL) was added and stirred for 10 minutes, and water (0.12 mL) was added and stirred for 10 minutes. The resultant solids were filtered and washed with chloroform (10 mL). The filtrate was concentrated under reduced pressure. The resulted residue was purified by silica gel column chromatography, (3% methanol/chloroform) to afford 2,5-dimethyl-6-{[4-(methylsulfanyl) phenyl] sulfanyl}-2,3,4,5-tetrahydro-1H-pyrido [4,3-b] indole (78 mg, 54%) as a pale-yellow colored oil. $^1$H NMR (CDCl$_3$, 300 MHz) δ 7.30 (d, 1H, J=7.3 Hz), 7.09-7.02 (m, 3H), 6.92-6.88 (m, 2H), 3.87 (s, 3H), 3.66 (s, 2H), 2.86-2.79 (m, 4H), 2.56 (s, 5H), 2.41 (s, 3H) ppm.

Step C. 2,5-Dimethyl-6-{[4-(methylsulfanyl)phenyl]sulfanyl}-2,3,4,5-tetrahydro-1H-pyrido[4,3-b]indole (0.078 g, 0.22 mmol) was dissolved in borane-tetrahydrofuran complex (3 mL) at room temperature and refluxed for 12 h. The reaction was cooled to rt and concentrated under reduced pressure to a slurry. To the slurry was added 6N HCl (3 mL), which was then heated at 90° C. for 12 h. The reaction mixture was cooled to room temperature and basified to pH 10 with concentrated ammonium hydroxide. This mixture was extracted with chloroform (3×75 mL). The combined organics were dried, filtered, and concentrated under reduced pressure. Purification of the resulted residue by silica gel column chromatography, (3% methanol, chloroform) afforded the title compound as a pale-yellow colored oil. $^1$H NMR (CDCl$_3$, 300 MHz) δ 7.22-7.14 (m, 4H), 7.03 (d, 2H, J=8.2 Hz), 6.92 (t, 1H, J=7.5 Hz), 4.23-4.20 (m, 1H), 3.80-3.70 (m, 1H), 3.60-3.50 (m, 1H), 3.48-3.31 (m, 1H), 3.22-3.17 (m, 1H), 3.09 (s, 3H), 2.99 (s, 3H), 2.42 (s, 3H) ppm.

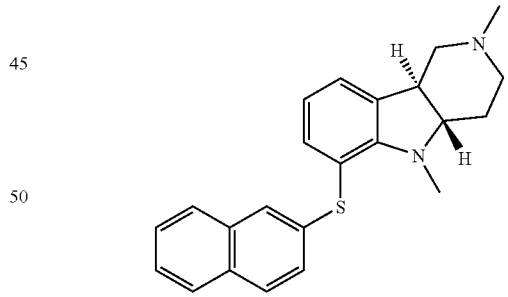

Example 10

Preparation of trans(4a,9b)-2,5-dimethyl-6-(2-naphthylsulfanyl)-2,3,4,4a,5,9b-hexahydro-1H-pyrido[4,3-b]indole Step A. Ethyl-5-methyl-6-(2-naphthylsulfanyl)-1,3,4,5-tetrahydro-2H-pyrido[4,3-b]indole-2-carboxylate was obtained by following the procedure of Example 9 step A, using the 2-naphthalenethiol. $^1$H NMR (CDCl$_3$, 300 MHz) δ 8.37 (d, 1H, J=9.2 Hz), 7.85 (d, 1H, J=9.5 Hz), 7.61-7.49 (m, 4H); 7.34 (d, 1H, J=7.3 Hz), 7.19 (t, 1H, J=7.7 Hz), 7.08 (t, 1H, J=7.7 Hz), 6.78 (d, 1H, J=7.3 Hz), 4.72 (s, 5H), 4.21 (q, 2H, J=7.2 Hz), 3.88 (s, 2H), 3.82 (s, 3H), 2.71 (s, 2H), 1.34-1.10 (m, 3H) ppm.

Step B. 2,5-dimethyl-6-(2-naphthylsulfanyl)-2,3,4,5-tetrahydro-1H-pyrido[4,3-b]indole (53 mg, 25%) was obtained by following the procedure of Example 9 step B. $^1$H NMR (CDCl$_3$, 300 MHz) δ 8.37 (d, 1H, J=9 Hz), 7.85 (d, 1H, J=9.5 Hz), 7.61-7.49 (m, 4H), 7.34 (d, 1H, J=7.3 Hz), 7.19 (t, 1H, J=7.7 Hz), 7.08 (t, 1H, J=7.8 Hz), 6.74 (d, 1H, J=7.3 Hz), 3.80 (s, 3H), 3.70 (s, 2H), 2.84-2.77 (m, 4H), 2.58 (s, 3H) ppm.

Step C. The title compound (24 mg, 41%) was prepared from 2,5-Dimethyl-6-(2-naphthylsulfanyl)-2,3,4,5-tetrahydro-1H-pyrido[4,3-b]indole by following the procedure of Example 9 Step C. $^1$H NMR (CDCl$_3$, 300 MHz) δ 8.32 (d, 1H, J=8.8 Hz), 7.86-7.83 (m, 1H), 7.66 (d, 1H, J=8.4 Hz), 7.57-7.48 (m, 2H), 7.31 (t, 1H, J=7.9 Hz), 7.11-7.01 (m, 3H), 6.73 (t, 1H, J=7.5 Hz), 3.57 (m, 1H), 3.13-3.07 (m, 1H), 3.04 (s, 3H), 2.88-2.76 (m, 1H), 2.59-2.48 (m, 1H), 2.45 (s, 3H), 2.27-2.02 (m, 3H), 1.87-182 (m, 1H) ppm.

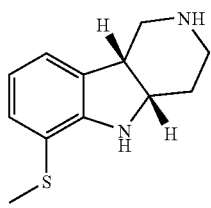

Example 11

Preparation of cis(4a,9b)-6-(methylsulfanyl)-2,3,4,4a,5,9b-hexahydro-1H-pyrido[4,3-b]indole Step A. 2-(Methylmercapto)aniline (23.6 g, 169.5 mmol) was suspended in conc. HCl (200 mL) and trifluoroacetic acid (130 mL), and cooled to 0° C. in an ice bath. Sodium nitrite (14.0 g, 203.4 mmol) was dissolved in water (45 mL) and added dropwise to the suspension over 45 minutes. After the addition, the reaction was stirred at 0° C. for 1 h. In a separate flask, tin (II) chloride (76 g, 338.4 mmol) was dissolved in conc. HCl (100 mL) and added slowly over 15 minutes to the reaction mixture. The resultant suspension was warmed to room temperature and stirred for 48 hours. The reaction was filtered, washed with isopropyl alcohol (15 mL), and dried to give 1-[2-(methylsulfanyl)phenyl]hydrazine hydrochloride (30 g, 93%). $^1$H NMR (CD$_3$OD, 300 MHz) δ 7.44 (d, 1H, J=7.7 Hz), 7.32-7.26 (m, 1H), 7.08-7.00 (m, 2H), 2.39 (s, 3H) ppm.

Step B. 1-[2-(methylsulfanyl)phenyl]hydrazine hydrochloride (27 g, 141.9 mmol) and 4-piperidone monohydrate hydrochloride (21.8 g, 141.9 mmol) were dissolved in ethanol (350 mL) and heated at reflux for 45 minutes. Concentrated HCl (30 mL) was added and heated at reflux for 12 h. The reaction was cooled to room temperature, filtered, washed with cold isopropyl alcohol (50 mL), and dried to give an off white solid, 6-(methylsulfanyl)-2,3,4,5-tetrahydro-1H-pyrido[4,3-b]indole hydrochloride (33 g, 92%). $^1$H NMR (CD$_3$OD, 300 MHz) δ 7.24 (d, 1H, J=8.7 Hz), 7.08 (dd, 1H, J=0.7, 7.3 Hz), 6.93 (t, 1H, J=7.7 Hz), 3.29-3.27 (m, 2H), 3.17 (t, 2H, J=5.85 Hz), 2.85 (t, 2H, J=5.65 Hz), 2.44 (s, 3H) ppm.

Step C. 6-(Methylsulfanyl)-2,3,4,5-tetrahydro-1H-pyrido[4,3-b]indole hydrochloride (20 g, 78.74 mmol) was suspended in trifluoroacetic acid (562 mL) and cooled to 0° C. in an ice bath. NaCNBH$_3$ (19.53 g, 314.96 mmol) was added portion wise over 25 minutes and the mixture was stirred at 0° C. for 4 h. The reaction mixture was basified to pH 10 with conc. ammonium hydroxide and extracted with ethyl acetate (4×500 mL) and the organic layer separated. The organics were collected, dried over magnesium sulfate, and filtered to give cis(4a,9b)-6-(methylsulfanyl)-2,3,4,4a,5,9b-hexahydro-1H-pyrido[4,3-b]indole. $^1$H NMR (CCl$_3$D, 300 MHz) δ 7.11 (d, 1H, J=7.7 Hz), 6.99 (d, 1H, J=7.3 Hz), 6.73 (t, 1H, J=5.7 Hz), 4.11 (s, 1H), 3.95-3.92 (m, 2H), 3.27-3.01 (m, 3H), 2.93-2.83 (m, 2H), 2.41 (s, 3H), 2.02-1.91 (m, 1H), 1.82-1.74 (m, 1H) ppm.

The following Examples 12 to 14 were prepared in good yields by the reaction of 2-chloronitrobenzene and the appropriate thiophenol as exemplified by the procedure of Example 2, followed by cis reduction as shown in Example 4.

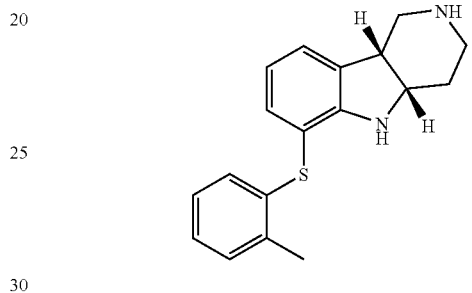

Example 12 cis(4a,9b)-6-[(2-Methylphenyl)sulfanyl]-2,3,4,4a,5,9b-hexahydro-1H-pyrido[4,3-b]indole $^1$H NMR, δ (CDCl$_3$) 7.20-7.00 (m, 5H), 6.80-6.75 (m, 2H), 4.05 (br s, 1H), 3.86 (q, 1H, J=5.5 Hz), 3.20 (q, 1H, J=6.3 Hz), 3.09 (dd, 1H, J=12.8, 5.5 Hz), 2.99-2.89 (m, 2H), 2.78-2.68 (m, 1H), 2.40 (s, 3H), 1.80-1.69 (m, 1H), 1.62-1.50 (m, 1H) ppm. 297.2 (M+H).

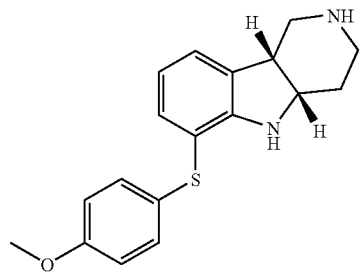

Example 13 cis(4a,9b)-6-[(4-Methoxyphenyl)sulfanyl]-2,3,4,4a,5,9b-hexahydro-1H-pyrido[4,3-b]indole $^1$H NMR, δ (CDCl$_3$) 7.14 (t, 3H, J=8.8 Hz), 7.07 (d, 1H, J=7.3 Hz), 6.81 (d, 2H, J=8.8 Hz), 6.71 (t, 1H, J=7.7 Hz), 4.07 (br s, 1H), 3.88 (q, 1H, J=5.5 Hz), 3.77 (s, 3H), 3.22-3.06 (m, 2H), 3.02-2.89 (m, 2H), 2.82-2.68 (m, 1H), 1.82-1.73 (m, 1H), 1.63-1.50(m, 1H) ppm. 313.1 (M+H).

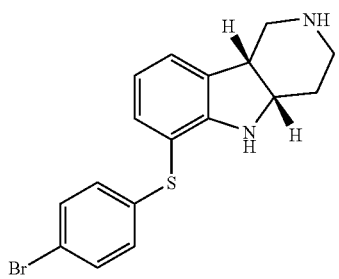

Example 14 cis(4a,9b)-6-[(4-Bromophenyl)sulfanyl]-2,3,4,4a,5, 9b-hexahydro-1H-pyrido [4,3-b]indole ¹H NMR, δ (CDCl₃) 7.34 (t, 2H, J=8.4 Hz), 7.22 (d, 1H, J=7.7 Hz), 7.15 (d, 2H, J=6.9 Hz), 6.77 (d, 1H, J=7.5 Hz), 4.12 (br s, 1H), 3.94 (q, 1H, J=5.5 Hz), 3.37-3.17 (m, 2H), 3.00-2.89 (m, 2H), 1.92-1.84 (m, 1H), 1.83-1.75 (m, 1H) ppm. 361.0 (M+H).

The following Examples 15-20 were prepared in good yields by the Fisher indole reaction of 1-methyl-4-piperidone hydrochloride reaction and the appropriate Thiophenylphenylhdrazin as exemplified by the procedure of Example 2, followed by trans reduction as shown in Example 1.

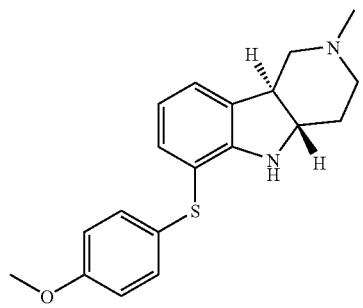

Example 15 trans(4a,9b)-6-[(4-Methoxyphenyl)sulfanyl]-2-methyl-2,3,4,4a,5,9b-hexahydro-1H-pyrido [4,3-b]indole ¹H NMR, δ (CD₃OD) 7.40 (d, 1H, J=7.3 Hz), 7.20-7.00 (m; 5H), 6.85-6.75 (m, 1H), 4.40 (br s, 1H), 4.20-4.12 (m, 1H), 3.74 (s, 3H), 3.69-3.54 (m, 2H), 3.18-3.08 (m, 2H), 2.93 (s, 3H), 2.32-2.28 (m, 1H), 2.10-2.01 (m, 1H) ppm.

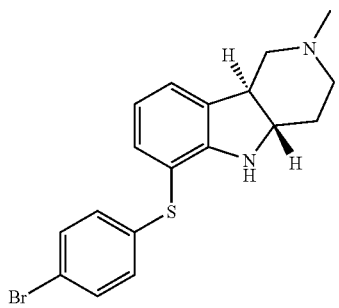

Example 16 trans(4a,9b)-6-[(4-Bromophenyl)sulfanyl]-2-methyl-2,3,4,4a,5,9b-hexahydro-1H-pyrido [4,3-b]indole ¹H NMR, δ (CD₃OD) 7.58 (d, 1H, J=7.5 Hz), 7.34 (d, 2H, J=8.2 Hz), 6.95 (d, 1H, J=8.5 Hz), 6.91 (d, 1H, J=7.0 Hz), 6.80 (t, 1H, J=7.0 Hz), 4.43 (br s, 1H), 4.18-4.12 (m, 1H), 3.65-3.55 (m, 2H), 3.16-2.97 (m, 2H), 2.93 (s, 3H), 2.33-2.28 (m, 1H), 2.08-2.00 (m, 1H) ppm. 375.1 (M+H).

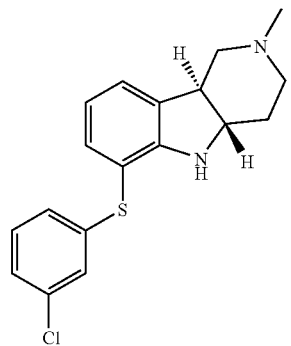

Example 17 trans(4a,9b)-6-[(3-Chlorophenyl)sulfanyl]-2-methyl-2,3,4,4a,5,9b-hexahydro-1H-pyrido[4,3-b]indole ¹H NMR, δ (CD₃OD) 7.30 (d, 2H, J=7.7 Hz), 7.24-7.08 (m, 4H), 7.04 (d, 1H, J=7.7 Hz), 4.25 (d, 1H, J=10.5 Hz), 3.72 (d, 1H, J=11.0 Hz), 3.60-3.50 (m, 2H), 3.40 (t, 1H, J=10.7 Hz), 3.30-3.19 (m, 1H), 2.99 (s, 3H), 2.45-2.37 (m, 1H), 2.30-2.15 (m, 1H) ppm. 361.0 (M+H).

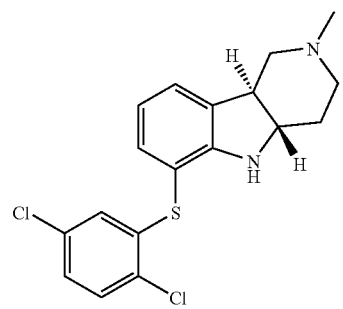

Example 18 trans(4a,9b)-6-[(2,6-Dichlorophenyl)sulfanyl]-2-methyl-2,3,4,4a,5,9b-hexahydro-1H-pyrido[4,3-b] indole ¹HNMR, δ (CDCl₃) 7.37 (d, 2H, J=7.7 Hz), 7.18 (t, 1H, J=7.4 Hz), 6.97 (d, 1H, J=8.0 Hz), 6.91 (d, 1H, J=7.0 Hz), 6.64 (t, 1H, J=7.7 Hz), 3.49 (dd, 1H, J=10.6, 2.5 Hz), 3.12-3.00 (m, 2H), 2.97 (dt, 1H, J=10.6, 2.9 Hz), 2.43 (s, 3H), 2.27 (t, 1H, J=10.6 Hz), 2.23-2.05 (m, 3H) ppm.

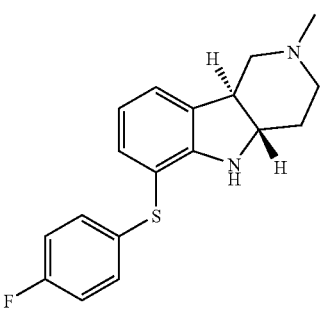

Example 19 trans(4a,9b)-6-[(4-Fluorophenyl)sulfanyl]-2-methyl-2,3,4,4a,5,9b-hexahydro-1H-pyrido[4,3-b]indole ¹H NMR, δ (CD₃OD) 7.16-6.93 (m, 6H), 6.72 (t, 1H, J=7.5 Hz), 3.51-3.44 (m, 1H), 3.08-2.95 (m, 2H), 2.89-2.79 (m, 1H), 2.38 (s, 3H), 2.28-2.00 (m, 3H), 1.91-1.80 (m, 2H) ppm.

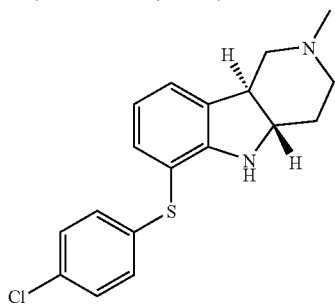

Example 20 trans(4a,9b)-6-[(4-Chlorophenyl)sulfanyl]-2-methyl-2,3,4,4a,5,9b-hexahydro-1H-pyrido [4,3-b]indole ¹H NMR, δ (CD₃OD) 7.20 (d, 4H, J=8.8 Hz), 7.15 (d, 2H, J=7.3 Hz), 7.04 (d, 2H, J=8.8 Hz), 6.80 (t, 1H, J=7.7 Hz), 4.13 (d, 1H, J=12.0 Hz), 3.58 (d, 1H, J=12.8 Hz), 3.32-2.95 (m, 4H), 2.91 (s, 3H), 2.30-2.02 (m, 1H), 2.10-2.00 (m, 1H) ppm. 331.1 (M+H)

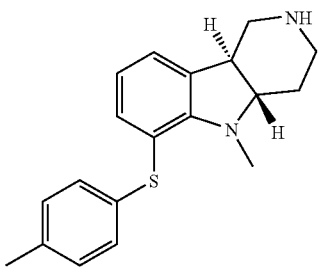

Example 21

Preparation of trans(4a,9b)-5-methyl-2,3,4,4a,5,9b-hexahydro-1H-pyrido[4,3-b]indol-6-yl-4-methylphenyl sulfide Step A. To a methylene chloride (300 mL) solution of 6-[(4-methylphenyl)sulfanyl]-2,3,4,5-tetrahydro-1H-pyrido[4,3-b]indole (71 mmol) was triethylamine (142 mmol) in one portion and resulted solution was stirred at rt for 10 minutes. The reaction was cooled to 0° C. in an ice bath then di-tert-butyl dicarbonate (85 mmol) was added, and then reaction was allowed to warm slowly to room temperature and stir for 14 hours. Reaction mixture was poured into water (300 ml) and then layers separated. The aqueous layer was extracted with chloroform (3×100 ml) and the organics collected, washed with brine (150 ml), dried over MgSO₄, and concentrated to dryness under reduced pressure to give tert-butyl 6-[(4methylphenyl)sulfanyl]-1,3,4,5-tetrahydro-2H-pyrido[4,3-b]indole-2-carboxylate (90%).

Step B. Tert-butyl 6-[(4-methylphenyl)sulfanyl]-1,3,4,5-tetrahydro-2H-pyrido[4,3-b]indole-2-carboxylate (22.6 mmol), potassium hydroxide (113 mmol), and iodomethane (226 mmol) were combined with dry DME (110 mL) and stirred at room temperature for 10 hours. The reaction was then filtered and the residue washed with chloroform. The filtrate was concentrated under reduced pressure to give tert-butyl 5-methyl-6-[(4-methylphenyl)sulfanyl]-1,3,4,5,-tetrahydro-2H-pyrido[4,3-b]indole-2-carboxylate (95%).

Step C. tert-Butyl 5-methyl-6-[(4-methylphenyl)sulfanyl]-1,3,4,5,-tetrahydro-2H-pyrido[4,3-b]indole-2-carboxylate was trans-reduced as shown in Example 1 to afford the title compound in good yield. ¹H NMR (300 MHz, CDCl₃) δ 7.07 (d, 1H, J=8 Hz), 6.99-6.88 (m, 5H), 6.67 (t, 1H, J=7.6 Hz), 3.54 (d, 1H, J=10.2), 3.14 (d, 1H, J=13.2), 2.95 (s, 3H), 2.67-2.45 (m, 4H), 2.19 (s, 3H), 2.03 (dd, 1H, J=2.2, 11.7 Hz), 1.59-1.50 (m, 1H) ppm.

The following Examples 22 to 30 were prepared in good yields by treatment of trans(4a,9b)-5-methyl-2,3,4,4a,5,9b-hexahydro-1H-pyrido[4,3-b]indol-6-yl-4-methylphenyl sulfide with the appropriate alkyl bromide as exemplified by the procedure of Example 6.

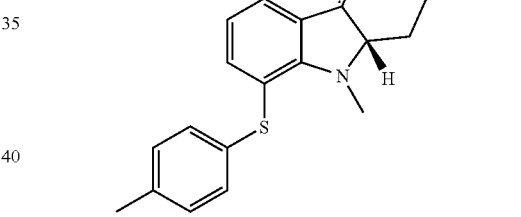

Example 22 trans(4a,9b)-2-(Cyclobutylmethyl)-5-methyl-6-[(4-methylphenyl)sulfanyl]-2,3,4,4a,5,9b-hexahydro-1H-pyrido[4,3-b]indole ¹H NMR, δ (CDCl₃) 7.10 (d, 1H, J=8.1 Hz), 7.04-7.00 (m, 3H), 6.91 (d, 2H, J=8.1 Hz), 6.72 (t, 1H, J=7.5 Hz), 3.50 (dd, 1H, J=2.2, 10.6 Hz), 3.10-3.06 (m, 1H), 2.99 (s, 3H), 2.67-2.57 (m, 4H), 2.24 (s, 3H), 2.21-1.67 (m, 10H) ppm.

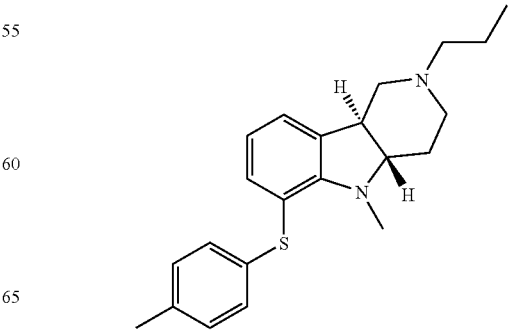

Example 23 trans(4a,9b)-5-Methyl-2-propyl-2,3,4,4a,5,9b-hexahydro-1H-pyrido [4,3-b]indol-6-yl 4-methylphenyl sulfide $^1$H NMR, δ (CDCl$_3$) 7.13 (d, 1H, J=8.1 Hz), 7.06-6.98 (m, 5H), 6.72 (t, 1H, J=7.4 Hz), 3.50 (dd, 1H, J=2.6, 10.6 Hz), 3.13 (d, 1H, J=11.7 Hz), 3.06 (s, 3H), 2.80 (t, 1H, J=11.9 Hz), 2.53-2.43 (m, 3H), 2.28 (s, 3H), 2.21-2.01 (m, 3H), 1.87-1.72 (m, 1H), 1.66-1.54 (m, 2H), 0.94 (t, 3H, J=7.5 Hz) ppm.

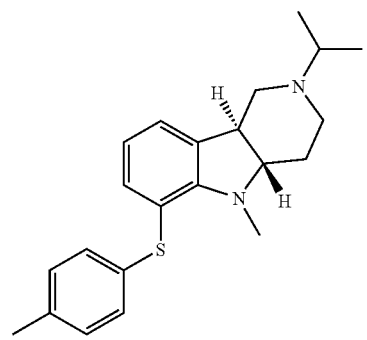

Example 24 trans(4a,9b)-2-Isopropyl-5-methyl-6-[(4-methylphenyl)sulfanyl]-2,3,4,4a,5,9b-hexahydro-1H-pyrido[4,3-b]indole $^1$H NMR, δ (CDCl$_3$) 7.13 (d, 1H, J=8 Hz), 7.06-6.98 (m, 5H), 6.72 (t, 1H, J=7.4 Hz), 3.46 (d, 1H, J=7.7 Hz), 3.09-2.77 (m, 6H), 2.50-2.33 (m, 3H), 2.28 (s, 3H), 2.10-2.03 (m, 1H), 1.85-1.70 (m, 1H), 1.12 (t, 6H, J=7.1 Hz) ppm.

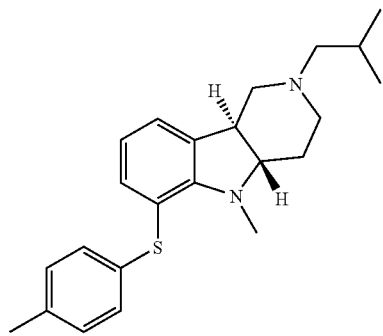

Example 25 trans(4a,9b)-2-Isobutyl-5-methyl-6-[(4-methylphenyl)sulfanyl]-2,3,4,4a,5,9b-hexahydro-1H-pyrido[4,3-b]indole $^1$H NMR, δ (CDCl$_3$) 7.15 (d, 1H, J=8.1 Hz), 7.06-6.97 (m, 5H), 6.72 (t, 1H, J=7.4 Hz), 3.47 (dd, 1H, J=2.6, 10.2 Hz), 3.11-3.03 (m, 4H), 2.83 (t, 1H, J=11.3 Hz), 2.48 (td, 1H, J=3.4, 12.3 Hz), 2.29 (s, 3H), 2.26-1.87 (m, 5H), 1.84-1.78 (m, 2H), 0.94 (d, 6H, J=6.6 Hz) ppm.

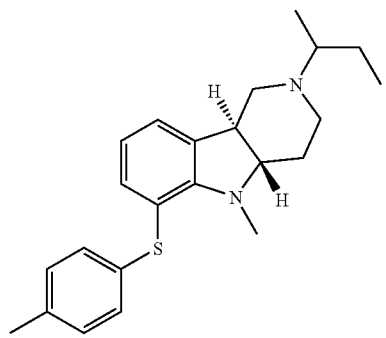

Example 26 trans(4a,9b)-2-sec-Butyl-5-methyl-6-[(4-methylphenyl)sulfanyl]-2,3,4,4a,5,9b-hexahydro-1H-pyrido[4,3-b]indole $^1$H NMR, δ (CDCl$_3$) 7.14 (d, 1H, J=8 Hz), 7.06-6.98 (m, 5H), 6.72 (t, 1H, J=7.5 Hz), 3.40 (m, 1H), 3.05 (s, 3H), 2.99-2.33 (m, 6H), 2.28 (s, 3H), 2.07-1.23 (m, 5H), 1.04 (t, 2H, J=6.6 Hz), 0.928 (t, 3H, J=7.3 Hz) ppm.

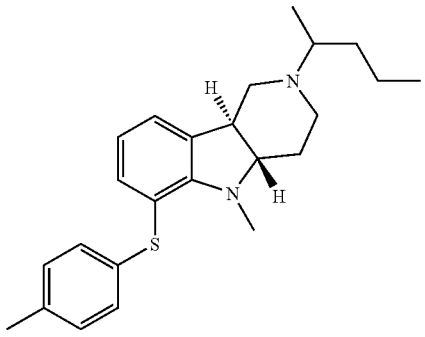

Example 27 trans(4a,9b)-5-Methyl-2-(1-methylbutyl)-6-[(4-methylphenyl)sulfanyl]-2,3,4,4a,5,9b-hexahydro-1H-pyrido[4,3-b]indole $^1$H NMR, δ (CDCl$_3$) 7.14 (d, 1H, J=8.1 Hz), 7.06-6.98 (m, 5H), 6.72 (t, 1H, J=7.5 Hz), 3.33 (d, 1H, J=7.7 Hz), 3.04 (s, 3H), 2.96-2.89 (m, 1H), 2.80-2.67 (m, 1H), 2.58-2.31 (m, 4H), 2.06-2.01 (m, 1H), 1.80-1.50 (m, 2H), 1.48-1.21 (m, 3H), 1.02 (t, 3H, J=6.4 Hz), 0.92 (t, 3H, J=6.1 Hz) ppm.

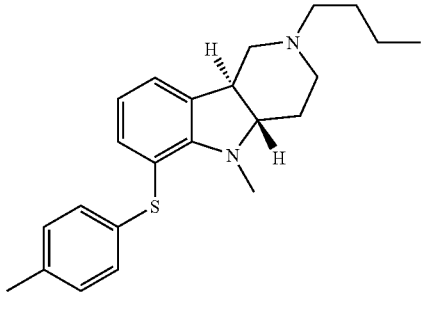

Example 28 trans(4a,9b)-2-Butyl-5-methyl-6-[(4-methylphenyl)sulfanyl]-2,3,4,4a,5,9b-hexahydro-1H-pyrido[4,3-b]indole $^1$H NMR, δ (CDCl$_3$) 7.15 (d, 1H, J=8.1 Hz), 7.06-6.97 (m, 5H), 6.72 (t, 1H, J=7.6 Hz), 3.62 (d, 1H, J=8.1 Hz), 3.26 (d, 1H, J=10.7 Hz), 3.06 (s, 3H), 2.92-2.82 (m, 1H), 2.71-2.43 (m, 4H), 2.28 (s, 3H), 2.25-2.18 (m, 1H), 2.14-2.03 (m, 1H), 2.01-1.81 (m, 1H), 1.69-1.51 (m, 2H), 1.47-1.28 (m, 2H), 0.96 (t, 3H, J=7.3 Hz) ppm.

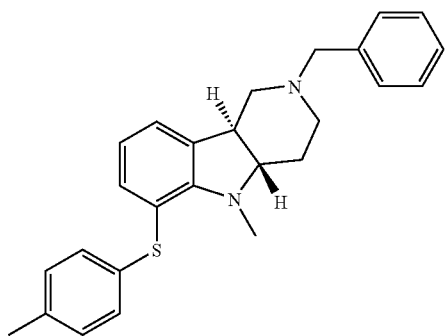

Example 29 trans(4a,9b)-2-Benzyl-5-methyl-6-[(4-methylphenyl)sulfanyl]-2,3,4,4a,5,9b-hexahydro-1H-pyrido[4,3-b]indole $^1$H NMR, δ (CD$_3$OD) 7.67 (br s, 2H), 7.53-7.42 (m, 3H), 7.33-7.71 (m, 7H), 4.51 (br s, 2H), 4.31-4.21 (m, 1H), 3.99-3.85 (m, 1H), 3.80-3.70 (m, 1H), 3.68-3.36 (m, 1H), 3.19 (s, 3H), 2.50 (br s, 2H), 2.31 (s, 3H), 1.43 (dd, 2H. J=6.6, 16.5 Hz) ppm.

Example 30 trans(4a,9b)-5-Methyl-2-(4-pentenyl)-2,3,4,4a,5,9b-hexahydro-1H-pyrido[4,3-b]indol-6-yl 4-methylphenyl sulfide $^1$H NMR, δ (CD$_3$OD) 7.36-7.713 (m, 7H), 5.90-5.80 (m, 1H), 5.16-5.03 (m, 2H), 4.90 (s, 3H), 4.45 (d, 1H, J=10 Hz), 3.93-3.80 (m, 3H), 3.45-3.32 (m, 2H), 3.24-3.20 (m, 3H), 2.50 (s, 2H), 2.32 (s, 3H), 2.20 (q, 2H, J=6.7 Hz), 2.02-1.95 (m, 2H) ppm.

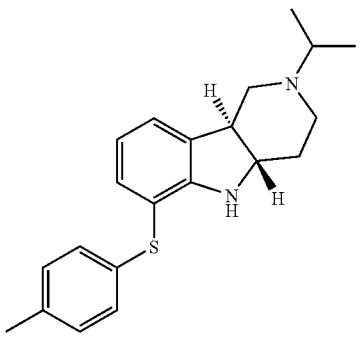

Example 31 trans(4a,9b)-2-Isopropyl-6-[(4-methylphenyl)sulfanyl]-2,3,4,4a,5,9b-hexahydro-1H-pyrido[4,3-b]indole The title compound was prepared in good yields by treatment of trans-6-[(4-methylphenyl)sulfanyl]-2,3,4,4a,5,9b-hexahydro-1H-pyrido[4,3-b]indole with 2-bromopropane as exemplified by the procedure of Example 6. $^1$H NMR, δ (CDCl$_3$) 7.15 (d, 1H, J=7.7 Hz), 7.05-7.03 (m, 5H), 6.75 (t, 1H, J=7.7 Hz), 4.43 (s, 1H), 3.49-3.40 (m, 1H), 3.01-2.89 (m, 3H), 2.58-2.29 (m, 1H), 2.28 (s, 3H), 2.03-1.98 (m, 1H), 1.23 (t, 6H, J=7.1 Hz) ppm.

The following Examples 32 to 38 were prepared in good yields by treatment of trans(4a,9b)-6-iodo-2,5-dimethyl-2,3,4,4a,5,9b-hexahydro-1H-pyrido[4,3-b]indole with the appropriate thiophenol as exemplified by the procedure of Example 8.

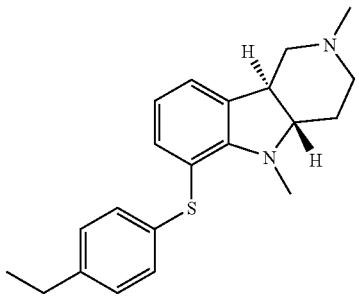

Example 32 trans(4a,9b)-6-[(4-Ethylphenyl)sulfanyl]-2,5-dimethyl-2,3,4,4a,5,9b-hexahydro-1H-pyrido [4,3-b]indole $^1$H NMR, δ (CDCl$_3$) 7.16 (d, 1H, J=8.2 Hz), 7.06 (s, 4H), 7.00 (d, 1H, J=8.0 Hz), 6.75 (t, 1H, J=8.0 Hz), 3.46 (dd, 1H, J=10.6, 2.5 Hz), 3.12-3.04 (m, 1H), 3.08 (s, 3H), 2.84 (dt, 1H, J=10.7, 2.5 Hz), 2.58 (q, 2H, J=7.3 Hz), 2.50 (dd, 1H, J=11.4, 3.3 Hz), 2.44 (s, 3H), 2.21 (t, 1H, J=10.6 Hz), 2.14-2.03 (m, 2H), 1.85 (dq, 1H, J=11.4, 3.7 Hz), 1.20 (t, 3H, J=7.7 Hz) ppm. 339.3 (M+H).

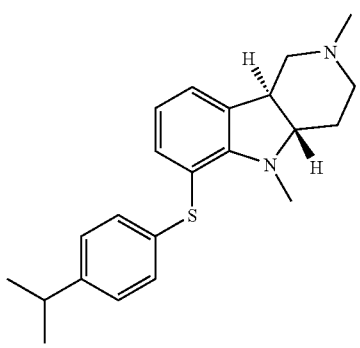

Example 33 trans(4a,9b)-6-[(4-Isopropylphenyl)sulfanyl]-2,5-dimethyl-2,3,4,4a,5,9b-hexahydro-1H-pyrido [4,3-b]indole $^1$H NMR, δ (CDCl$_3$) 7.43 (d, 1H, J=8.5 Hz), 7.23-6.95 (m, 4H), 6.81-6.70 (m, 2H), 3.51 (dd, 1H, J=11.0, 2.5 Hz), 3.15-3.08 (m, 1H), 3.08 (s, 3H), 2.94-2.80 (m, 2H), 2.52-2.48 (m, 1H), 2.48 (s, 3H), 2.30-2.10 (m, 2H), 2.09-2.00 (m, 1H), 1.95-1.80 (m, 1H), 1.20 (d, 6H, J=7.0 Hz) ppm. 353.3 (M+H).

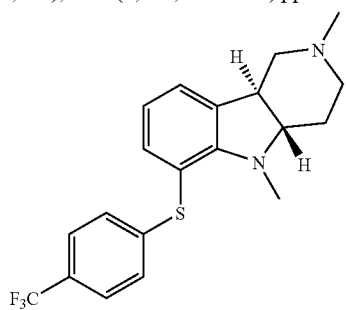

Example 34 trans(4a,9b)-2,5-dimethyl-6-{[4-(trifluoromethyl)phenyl]sulfanyl}-2,3,4,4a,5,9b-hexahydro-1H-pyrido[4,3-b]indole $^1$H NMR, δ (CDCl$_3$) 7.44 (d, 1H, J=8.4 Hz), 7.11-7.04 (m, 4H), 6.79 (t, 1H, J=7.3 Hz), 3.47 (dd, 1H, J=10.5, 2.4 Hz), 3.00 (s, 3H), 2.92-2.80 (m, 2H), 2.57-2.48 (m, 2H), 2.45 (s, 3H), 2.23 (t, 1H, J=10.3 Hz), 2.17-2.00 (m, 1H), 1.90-1.80 (m, 1H) ppm.

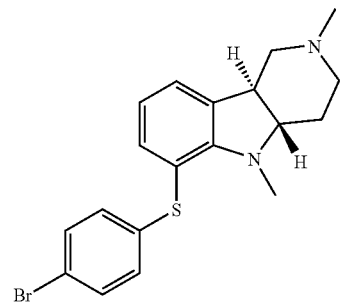

Example 35 trans(4a,9b)-6-[(4-Bromophenyl)sulfanyl]-2,5-dimethyl-2,3,4,4a,5,9b-hexahydro-1H-pyrido[4,3-b]indole $^1$H NMR, δ (CD$_3$OD) 7.39 (d, 2H, J=8.5 Hz), 7.25 (t, 3H, J=8.1 Hz), 6.99 (d, 2H, J=8.4 Hz), 4.25 (d, 1H, J=11.4 Hz), 3.74 (d, 1H, J=9.9 Hz), 3.49-3.31 (m, 2H), 3.21-3.18 (m, 2H), 3.07 (s, 3H), 2.99 (s, 3H), 2.42 (d, 1H, J=13.5 Hz), 2.18-2.00 (m, 1H) ppm.

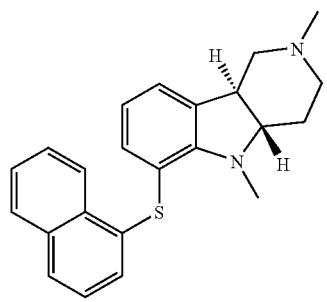

Example 36 trans(4a,9b)-2,5-Dimethyl-6-(1-naphthylsulfanyl)-2,3,4,4a,5,9b-hexahydro-1H-pyrido[4,3-b]indole $^1$H NMR, δ (CDCl$_3$) 7.76-7.63 (m, 3H), 7.56-38 (m, 3H), 7.31-7.23 (m, 2H), 7.06 (d, 1H, J=7 Hz), 6.78 (t, 1H, J=7.5 Hz), 3.57-3.40 (m, 1H), 3.06 (s, 3H), 2.94-2.79 (m, 2H), 2.60-2.44 (m, 4H), 2.28-2.00 (m, 3H), 1.92-1.82 (m, 1H) ppm.

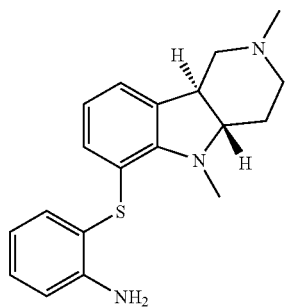

Example 37

4-{[trans(4a,9b)-2,5-Dimethyl-2,3,4,4a,5,9b-hexahydro-1H-pyrido[4,3-b]indol-6-yl]sulfanyl}aniline $^1$H NMR, δ (CDCl$_3$) 7.13-7.09 (m, 2H), 6.95 (dt, 1H, J=7.7, 11.5 Hz), 6.88 (dt, 1H, J=7.5, 11.2 Hz), 6.69-6.59 (m, 3H), 3.68 (s-broad, 2H), 3.47 (d, 1H, J=11.4 Hz), 3.15-3.06 (m, 4H), 2.85-2.81 (m, 1H), 2.49-2.40 (m, 4H), 2.21-2.05 (m, 3H), 1.89-1.84 (m, 1H) ppm.

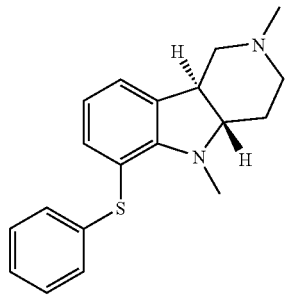

Example 38 trans(4a,9b)-2,5-Dimethyl-6-(phenylsulfanyl)-2,3,4,4a,5,9b-hexahydro-1H-pyrido[4,3-b]indole $^1$H NMR, δ (CDCl$_3$) 7.21 (t, 3H, J=7.0 Hz), 7.12-7.07 (m, 3H), 7.02 (d, 1H, J=7.3 Hz), 6.75 (t, 1H, J=7.3 Hz), 3.44 (dd, 1H, J=11.5, 2.5 Hz), 3.07 (d, 1H, J=11.5 Hz), 3.05 (s, 3H), 2.83 (dt, 1H, J=10.3, 3.7 Hz), 2.50 (dd, 1H, J=11.4, 3.3 Hz), 2.43 (s, 3H), 2.20 (t, 1H, J=10.6 Hz), 2.14-2.02 (m, 2H), 1.88-1.79 (m, 1H) ppm. 311.2 (M+H)

The following Examples 39 to 40 were prepared in good yields by treatment of ethyl 6-iodo-1,3,4,5-tetrahydro-2H-pyrido[4,3-b]indole-2-carboxylate with the appropriate thiophenol as exemplified by the procedure of Example 14, followed by reduction of the ethylcarboxylate as per example 10 step F, and trans reduction of the indole to the title compound via Example 1.

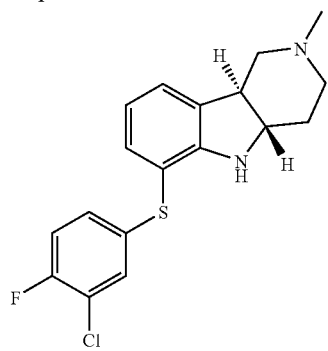

Example 39 trans(4a,9b)-6-[(3-Chloro-4-fluorophenyl)sulfanyl]-2-methyl-2,3,4,4a,5,9b-hexahydro-1H-pyrido[4,3-b]indole $^1$H NMR, δ (CDCl$_3$) 7.80-7.60 (m, 2H), 7.57-7.37 (m, 2H), 7.20-711 (m, 1H), 6.80 (t, 1H, J=7.5 Hz), 3.51-3.44 (m, 1H), 3.08-2.95 (m, 2H), 2.89-2.79 (m, 1H), 2.41 (s, 3H), 2.28-2.00 (m, 3H), 1.91-1.80 (m, 2H) ppm.

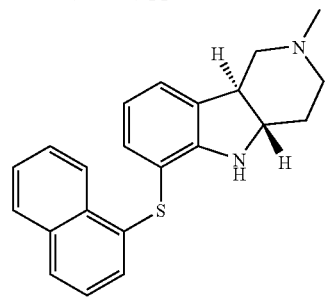

Example 40 trans(4a,9b)-2-Methyl-6-(2-naphthylsulfanyl)-2,3,4,4a,5,9b-hexahydro-1H-pyrido[4,3-b]indole $^1$H NMR, δ (CD$_3$OD) 7.16 (d, 1H, J=8.1), 7.06-6.83 (m, 1H), 6.82-6.72 (m, 4H), 4.57 (s-broad, 2H), 3.44-3.40 (m, 1H), 3.03-2.91 (m, 3H), 2.42 (s, 3H), 2.36-2.18 (m, 2H) ppm.

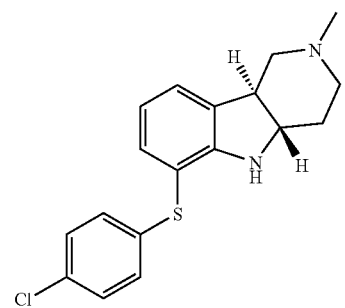

Example 41

Preparation of trans(4a,9b)-6-[(4-chlorophenyl)sulfanyl]-2,5-dimethyl-2,3,4,4a,5,9b-hexahydro-1H-pyrido[4,3-b]indole The title compound was prepared from 4-chlorophenyl 5-methyl-2,3,4,5-tetrahydro-1H-pyrido[4,3-b]indol-6-yl sulfide by the procedure of Example 9. $^1$H NMR (300 MHz, CD$_3$OD) δ 7.28-7.15 (m, 4H), 6.96 (d, 2H, J=8.8 Hz), 6.87 (t, 1H, J=7.5 Hz), 4.21 (d, 1H, J=12.0 Hz), 3.76-3.70 (m, 1H), 3.56-3.10 (m, 3H), 3.04 (s, 3H), 2.99 (s, 3H), 2.90-2.81 (m, 2H), 2.47-2.37 (m, 1H) ppm. MS (EI) 345.2 (M+H).

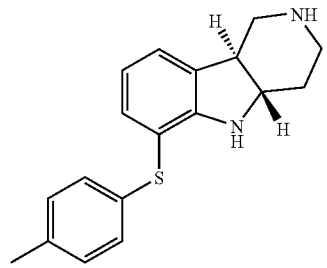

Example 42

Preparation of trans(4a,9b)-6-[(4-methylphenyl)sulfanyl]-2,3,4,4a,5,9b-hexahydro-1H-pyrido [4,3-b] indole The title compound was prepared by reduction of 4-methylphenyl-2,3,4,5-tetrahydro-1H-pyrido[4,3-b]indol-6-yl sulfide hydrochloride as per the procedure of Example 1. $^1$H NMR (300 MHz, CD$_3$OD) δ 7.42 (d, 1H, J=7.8 Hz), 7.19 (d, 1H, J=7.3 Hz), 7.02 (t, 1H, J=7.3 Hz), 6.96 (s, 4H), 4.20 (d, 1H, J=10.8 Hz, 3.75 (d, 1H, J=11.0 Hz), 3.30-3.25 (m, 2H), 3.05-2.78 (m, 3H), 2.22 (s, 3H) ppm.

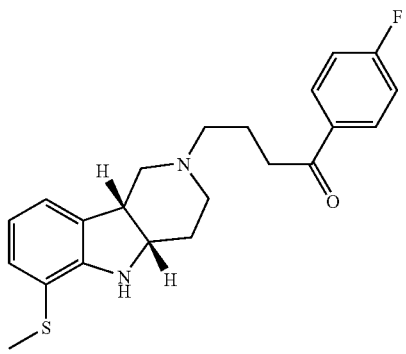

Example 43

4-[cis(4a,9b)-6-(Methylsulfanyl)-1,3,4,4a,5,9b-hexahydro-2H-pyrido [4,3-b]indol-2-yl]-1-(4-fluorophenyl)-1-butanone The title compound was prepared in good yields by alkylation of cis(4a,9b)-6-(methylsulfanyl)-2,3,4,4a,5,9b-hexahydro-1H-pyrido[4,3-b]indole with 4-chloro-1-(4-fluorophenyl)-1-butanone as per example 6. $^1$H NMR, 8.00-7.95 (m, 2H), 7.14-7.08 (m, 3H), 6.97 (d, 1H, J=7.3 Hz), 6.69 (t, 1H, J=7.3 Hz), 4.05-4.00 (br s, 1H), 3.88-3.79 (m, 1H), 3.17 (q, 1H, J=6.6 Hz), 2.97 (t, 2H, J=7.4 Hz), 2.66 (dd, 1H, J=11.7, 6.9 Hz), 2.50-2.35 (m, 4H), 2.39, (s, 3H), 2.29 (dd, 1H, J=11.7, 8.8 Hz), 2.00-1.75 (m, 4H) ppm. 385.1 (M+H).

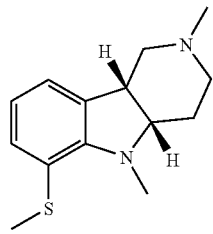

Example 44

Preparation of cis(4a,9b)-2,5-dimethyl-6-[(4-methylphenyl)sulfanyl]-2,3,4,4a,5,9b-hexahydro-1H-pyrido[4,3-b]indole The title compound was prepared from the 1-methyl-4-piperidone hydrochloride and corresponding hydrazine as exemplified by the procedure of Example 2, followed by cis reduction as shown in Example 4. $^1$H NMR (300 MHz, CDCl$_3$) δ 7.17 (d, 1H, J=8.0 Hz), 7.06 (d, 1H, J=7.7 Hz), 7.04 (d, 2H, J=8.4 Hz), 6.97 (d, 2H, J=8.4 Hz), 6.69 (t, 1H, J=7.3 Hz), 3.28-3.20 (m, 2H), 3.04 (s, 3H). 2.75-2.65 (m, 1H), 2.50-2.46 (m, 1H), 2.28 (s, 3H), 2.27 (s, 3H), 2.21-1.95 (m, 1H), 1.96-1.91 (m, 3H) ppm.

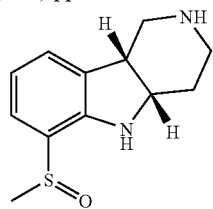

Example 45

Preparation of cis(4a,9b)-6-(methylsulfinyl)-2,3,4,4a,5,9b-hexahydro-1H-pyrido[4,3-b]indole Step A. C is(4a, 9b)-6-(methylsulfanyl)-2,3,4,4a,5,9b-hexahydro-1H-pyrido[4,3-b]indole (from Example 11, Step C) (8.0 g, 36.2 mmol), triethylamine (5 ml), and di-tert-butyl dicarbonate (8.68 g, 39.8 mmol) were dissolved in chloroform (180 ml) stirred for 6 hours. Reaction was concentrated under reduced pressure. The resulted residue was mixed with (7.9 g, 36.2 mmol) of di-tert-butyl dicarbonate, neat and heated at 120° C. for 12 hours. The resultant residue was purified by silica gel column eluting with 15% ethylacetate/hexanes to give di(tert-butyl) cis(4a, 9b)-6-(methylsulfanyl)-3,4,4a,9b-tetrahydro-1H-pyrido[4,3-b]indole-2,5-dicarboxylate as a white foam (2.10 g, 14%). $^1$H NMR (DMSO, 300 MHz) δ 7.21-7.19 (μ, 1H), 7.07-7.02 (m, 2H), 4.63-4.59 (m, 1H), 4.21-4.17 (m, 1H), 3.69-3.62 (m, 1H), 3.50-3.39 (m, 2H), 2.97-2.89 (m, 2H), 2.34 (s, 3H), 2.00-1.94 (m, 1H), 1.49 (s, 9H), 1.34 (s, 9H) ppm.

Step B. Di(tert-butyl) cis(4a, 9b)-6-(methylsulfanyl)-3,4,4a,9b-tetrahydro-1H-pyrido[4,3-b]indole-2,5-dicarboxylate (0.043 mmol) was dissolved in MeOH/H$_2$O (2.5/1 ml) and cooled in an ice bath to 0° C. under a nitrogen atmosphere. Sodium periodate (0.043 mmol) was added in one portion, and reaction was stirred at 0° C. for 4 hours. After 4 hours, reaction was allowed to warm to room temperature and stir for 12 hours. Reaction solution was filtered and concentrated to an aqueous slurry, which was diluted with brine (5 ml) and then extracted (3×15 ml) with CHCl$_3$. The organics were collected, dried over MgSO$_4$ and concentrated under reduced pressure to give a white solid. It was then dissolved in 20% TFA/CHCl$_3$ and stirred for 1 hour. The reaction solution was cooled to 0° C. in an ice bath, and basified to pH=10 with concentrated NH$_4$OH. This was extracted with CHCl$_3$ (3×15 ml), organics collected, dried over MgSO$_4$ and concentrated under reduced pressure to give the title compound (71%). $^1$H NMR (CD$_3$OD, 300 MHz) □ 7.19 (d, 1H, J=6.9 Hz), 7.07 (d, 1H, J=7.7 Hz), 6.77 (t, 1H, J=7.7 Hz), 5.56 (s, 1H), 3.94 (q, 1H, J=6.8 Hz), 3.37-3.34 (m,1H), 3.18-3.03 (m, 2H), 2.98-2.82 (m, 5H), 2.65-2.56 (m, 1H), 1.86-1.80 (m, 1H), 1.49-1.38 (m, 1H) ppm.

The Tables below provide representative Examples, the synthesis of which are described above, of the compounds of Formula (I) of the present invention.

TABLE 1

| Ex # | X | R$^5$ | R$^6$ | Stereo | R$^1$ |
|---|---|---|---|---|---|
| 1 | S | H | 4-Me-Ph- | trans | Me |
| 2 | S | H | 4-F-Ph- | trans | Me |
| 3 | S | H | 4-Cl-Ph- | trans | Me |
| 4 | S | H | 4-Me-Ph- | cis | H |
| 5 | NH | Me | 4-Me-Ph- | trans | Me |
| 6 | S | H | 4-Me-Ph- | trans | —(CH$_2$)$_3$C(=O)(4-F-phenyl) |
| 7 | S | Me | 4-Me-Ph- | trans | Me |
| 8 | S | Me | 4-F-Ph- | trans | Me |
| 9 | S | Me | 4-MeS-Ph- | trans | Me |
| 10 | S | Me | 2-naphthyl | trans | Me |
| 11 | S | H | Me | cis | H |
| 12 | S | H | 2-Me-Ph- | cis | H |
| 13 | S | H | 4-MeO-Ph- | cis | H |
| 14 | S | H | 4-Br-Ph- | cis | H |
| 15 | S | H | 4-MeO-Ph- | trans | Me |
| 16 | S | H | 4-Br-Ph- | trans | Me |
| 17 | S | H | 3-Cl-Ph- | trans | Me |
| 18 | S | H | 2,5-diCl-Ph- | trans | Me |
| 19 | S | H | 4-F-Ph- | trans | Me |
| 20 | S | H | 4-Cl-Ph- | trans | Me |
| 21 | S | Me | 4-Me-Ph- | trans | H |
| 22 | S | Me | 4-Me-Ph- | trans | cyclobutylmethyl |
| 23 | S | Me | 4-Me-Ph- | trans | propyl |
| 24 | S | Me | 4-Me-Ph- | trans | i-propyl |
| 25 | S | Me | 4-Me-Ph- | trans | i-butyl |
| 26 | S | Me | 4-Me-Ph- | trans | 1-Me-propyl |
| 27 | S | Me | 4-Me-Ph- | trans | 1-Me-butyl |

TABLE 1-continued

[Structure diagram of a tricyclic compound with R¹ on top nitrogen, X-R⁶ substituent on benzene ring, and R⁵ on bottom nitrogen]

| Ex # | X    | R⁵ | R⁶         | Stereo | R¹                      |
|------|------|-----|------------|--------|-------------------------|
| 28   | S    | Me  | 4-Me-Ph-   | trans  | butyl                   |
| 29   | S    | Me  | 4-Me-Ph-   | trans  | benzyl                  |
| 30   | S    | Me  | 4-Me-Ph-   | trans  | 4-pentenyl              |
| 31   | S    | H   | 4-Me-Ph-   | trans  | i-propyl                |
| 32   | S    | Me  | 4-Et-Ph-   | trans  | Me                      |
| 33   | S    | Me  | 4-iPr-Ph-  | trans  | Me                      |
| 34   | S    | Me  | 4-CF₃-Ph-  | trans  | Me                      |
| 35   | S    | Me  | 4-Br-Ph-   | trans  | Me                      |
| 36   | S    | Me  | 1-naphthyl | trans  | Me                      |
| 37   | S    | Me  | 2-NH₂-Ph-  | trans  | Me                      |
| 38   | S    | Me  | Ph         | trans  | Me                      |
| 39   | S    | H   | 3-Cl-4-F-Ph- | trans | Me                     |
| 40   | S    | H   | 1-naphthyl | trans  | Me                      |
| 41   | S    | Me  | 4-Cl-Ph-   | trans  | Me                      |
| 42   | S    | H   | 4-Me-Ph-   | trans  | H                       |
| 43   | S    | H   | Me         | cis    | —(CH₂)₃C(=O)(4-F-phenyl) |
| 44   | S    | Me  | 4-Me-Ph-   | cis    | Me                      |
| 45   | S(=O)| H   | Me         | cis    | H                       |

Utility

The compounds of the present invention have therapeutic utility for illnesses or disorders involving the neurotransmitter serotonin (5-hydroxy tryptamine or 5-HT) and either agonism or antagonism of 5-HT2 receptors, as demonstrated by the assays described below. Therapeutic utility for these illnesses or disorders could involve numerous biological processes affected by serotonin including, but not limited to, appetite, mood, sleep, sexual activity, and arterial constriction. These biological processes may also be important to numerous central nervous system (CNS) disorders including those related to the affective disorders of depression, anxiety, psychosis, and schizophrenia, as well as, disorders of food intake such as anorexia, bulimia, and obesity. The compounds of the present invention potentially have therapeutic utility in other conditions in which serotonin has been implicated, such as migraine, attention deficit disorder or attention deficit hyperactivity disorder, addictive behavior, and obsessive-compulsive disorder, as well as, conditions associated with cephalic pain, social phobias, and gastrointestinal disorders such as dysfunction of the gastrointestinal tract motility. Lastly, compounds of the present invention potentially have therapeutic utility in neurodegenerative diseases and traumatic conditions represented by the examples of Alzheimer's disease and brain/spinal cord trauma.

The pharmacological analysis of each compound for either antagonism or agonism of at 5-HT2A and 5-HT2C receptors consisted of in vitro and in vivo studies. In vitro analyses included $K_i$ determinations at 5-HT2A and 5-HT2C receptors and an assessment of functional (i.e., agonism or antagonism) activity at each receptor class by IP3 hydrolysis assays. Additional receptor assays were conducted to evaluate receptor specificity of 5-HT2A and 5-HT2C receptors over monoamine and nuisance receptors (e.g. histamine, dopamine, and muscarinic). A compound is considered active as a 5-HT2A antagonist or a 5-HT2C agonist if it has an $IC_{50}$ value or a $K_i$ value of less than about 50 micromolar; preferably less than about 0.1 micromolar; more preferably less than about 0.01 micromolar. Using the assays disclosed herein, compounds of the present invention have been shown to have an $IC_{50}$ value of less than about 50 micromolar for 5-HT2A antagonism or 5-HT2C agonism.

In vivo assays assessed compound activity in a variety of behavioral paradigms including quipazine head twitch, acute and chronic feeding models, anxiety and depression models (learned-helplessness, elevated plus maze, Geller-Siefter, conditioned taste aversion, taste reactivity, satiety sequence). In aggregate, these models reflect activity as a 5-HT2A antagonist (quipazine head twitch, depression models) or 5-HT2C agonist (feeding models, anxiety models, depression models) and provide some indication as to bioavailability, metabolism and pharmacokinetics.

Radioligand binding experiments were conducted on recombinant human 5-HT2A and 5-HT2C receptors expressed in HEK293E cells. The affinities of compounds of the present invention to bind at these receptors is determined by their capacity to compete for [$^{125}$I]-1-(2,5-dimethoxy-4-iodophenyl)-2-amino-propane (DOI) binding at the 5-HT2A or 5-HT2C. General references for binding assays include 1) Lucaites V L, Nelson D L, Wainscott D B, Baez M (1996) Receptor subtype and density determine the coupling repertoire of the 5-HT2 receptor subfamily. Life Sci., 59(13):1081-95. J Med Chem 1988 January; 31(1):5-7; 2) Glennon R A, Seggel M R, Soine W H, Herrick-Davis K, Lyon R A, Titeler M (1988) [$^{125}$I]-1-(2,5-dimethoxy-4-iodophenyl)-2-amino-propane: an iodinated radioligand that specifically labels the agonist high-affinity state of 5-HT2 serotonin receptors. J. Med. Chem. 31(1):5-7 and 3) Leonhardt S, Gorospe E, Hoffman B J, Teitler M (1992) Molecular pharmacological differences in the interaction of serotonin with 5-hydroxytryptamine1C and 5-hydroxytryptamine2 receptors. Mol Pharmacol., 42(2):328-35.

The functional properties of compounds (efficacy and potency) were determined in whole cells expressing 5-HT2A or 5-HT2C receptors by assessing their ability to stimulate or inhibit receptor-mediated phosphoinositol hydrolysis. The procedures used are described below.

In Vitro Binding Assays

Stable expression of 5-HT2A and 5-HT2C receptors in HEK293E cells

Stable cell lines were generated by transfecting 293EBNA cells with plasmids containing human 5-HT2A, 5-HT2B, or 5-HT2C (VNV edited isoform) cDNA using calcium phosphate. These plasmids also contained the cytomegalovirus (CMV) immediate early promoter to drive receptor expression and EBV oriP for their maintenance as an extrachromosomal element, and the hph gene from *E. Coli* to yield hygromycin B resistance (Horlick et al., 1997). Transfected cells were maintained in Dulbecco's Modified Eagle medium (DMEM) containing dialyzed 10% fetal bovine serum at 37° C. in a humid environment (5% $CO_2$) for 10 days. The 5-HT2A cells were adapted to spinner culture for bulk processing whereas it was necessary to maintain the other lines as adherent cultures. On the day of harvest, cells were washed in phosphate-buffered saline (PBS), counted, and stored at −80° C.

Membrane Preparation

On the day of assay, pellets of whole cells (containing approximately 1×108 cells) expressing the 5-HT2A or 5-HT2C receptor were thawed on ice and homogenized in 50 mM Tris HCl (pH 7.7) containing 1.0 mM EDTA using a Brinkman Polytron (PT-10, setting 6 for 10 sec). The homogenate was centrifuged at 48,000×g for 10 min and the resulting pellet washed twice by repeated homogenization and centrifugation steps. The final pellet was resuspended in tissue buffer and protein determinations were made by the bichichoninic acid (BCA) assay (Pierce Co., IL) using bovine serum albumin as the standard.

Radioligand Binding Assays for the 5-HT2A, and 5-HT2C Receptors

Radioligand binding studies were conducted to determine the binding affinities (KI values) of compounds for the human recombinant 5-HT2A, 5-HT2B, and 5-HT2C receptors (Fitzgerald et al., 1999). Assays were conducted in disposable polypropylene 96-well plates (Costar Corp., Cambridge, Mass.) and were initiated by the addition of 5-HT2A, 5-HT2B, or 5-HT2C membrane homogenate in tissue buffer (10-30 (g/well) to assay buffer (50 mM Tris HCl, 0.5 mM EDTA, 10 mM pargyline, 10 mM $MgSO_4$, 0.05% ascorbic acid, pH 7.5) containing [$^{125}$I]DOI for the 5-HT2A and 5-HT2C receptors (0.3-0.5 nM, final) or [$^3$H]LSD (2-2.5 nM, final) for the 5-HT2B receptor, with or without competing drug (i.e., newly synthesized chemical entity). For a typical competition experiment, a fixed concentration of radioligand was competed with duplicate concentrations of ligand (12 concentrations ranging from 10 picomolar to 10 micromolar). The reaction mixtures were incubated to equilibrium for 45 min at 37° C. and terminated by rapid filtration (cell harvestor; Inotech Biosystems Inc., Lansing, Mich.) over GFF glass-fiber filters that had been pre-soaked in 0.3% polyethyleneimine. Filters were washed in ice-cold 50 mM Tris HCl buffer (pH 7.5) and then counted in a gamma counter for the 5-HT2A and 5-HT2C assays, or by liquid scintillation spectroscopy for the 5-HT2B assay.

Phosphoinositide Hydrolysis Studies

The ability of newly synthesized compounds to stimulate phosphoinositide (PI) hydrolysis was monitored in whole cells using a variant (Egan et al., 1998) of a protocol described previously (Berridge et al., 1982). HEK293E cells expressing the human 5-HT2A, 5-HT2B, or 5-HT2C receptor were lifted with 0.5 mM EDTA and plated at a density of 100,000/well onto poly-D-lysine-coated 24-well plates (Biocoat; Becton Dickinson, Bedford, Mass.) in Dulbecco's modified Eagle's serum (DMEM; Gibco BRL) containing high glucose, 2 mM glutamine, 10% dialyzed fetal calf serum, 250 (g/ml hygromycin B, and 250 (g/ml G418. Following a 24-48 hr period, the growth media was removed and replaced with DMEM without fetal calf serum and inositol (Gibco BRL). The cells were then incubated with DMEM (without serum and inositol) containing a final concentration of 0.5 uCi/well myo-[$^3$H] inositol for 16-18 hr. Following this incubation, the cells were washed with DMEM (without serum or inositol) containing 10 mM LiCl and 10 (M pargyline and then incubated for 30 min with the same media but now containing one of several test compounds. Reactions were terminated by aspirating the media and lysing the cells by freeze-thaw. [$^3$H]phosphoinositides were extracted with chloroform/methanol (1:2 v/v), separated by anion exchange chromatography (Bio-Rad AGI-X8 resin), and counted by liquid scintillation spectroscopy as described previously (Egan et al., 1998).

Data Analyses

The equilibrium apparent dissociation constants (Ki's) from the competition experiments were calculated using an iterative nonlinear regression curve-fitting program (GraphPad Prism; San Diego, Calif.). For the PI hydrolysis experiments, EC50's were calculated using a one-site 'pseudo' Hill model: $y=((Rmax-Rmin)/(1+R/EC50)_nH))+Rmax$ where R=response (DeltaGraph, Monterey, Calif.). Emax (maximal response) was derived from the fitted curve maxima (net IP stimulation) for each compound. Intrinsic activity (IA) was determined by expressing the Emax of a compound as a percentage of the Emax of 5-HT (IA=1.0).

In Vivo Experiments for Serotonergic Ligands

Preclinical Efficacy, Potency, and Side Effect Liability a) Anti-Serotonin Efficacy Antagonism of Quipazine-Induced Head Twitch in Rat. Quipazine, an agonist at 5-HT receptors, produces a characteristic head twitch response in rats. 5-HT receptor antagonists effectively antagonize this 5-HT agonist-induced behavioral effect (Lucki et al., 1984). Accordingly, the quipazine-induced head twitch model in rat can function as an in vivo behavioral correlate to 5-HT receptor binding. Compounds are administered 30 minutes before behavioral testing (and 25 minutes before quipazine), and a dose-related antagonism of the quipazine response is determined.

b) Antipsychotic Efficacy

Inhibition of the Conditioned Avoidance Response (CAR) in Rat. Rats are trained to consistently avoid (by climbing onto a pole suspended from the ceiling of the test chamber) an electric foot shock (0.75 mA) delivered to the grid floor of the testing chamber. All antipsychotic drugs effectively inhibit this conditioned avoidance response (Arnt, 1982). The ability of a compound to inhibit this response is used to determine the antipsychotic efficacy of potential drug candidates.

c) Extrapyramidal Side Effect Liability

Induction of Catalepsy in Rat. Typical antipsychotic drugs produce extrapyramidal side effects (EPS) at clinically effective doses. The most widely accepted preclinical indicator of EPS liability in humans is a drug-induced catalepsy syndrome in rat (Costall and Naylor, 1975), a condition whereby the animal will remain immobile in an externally imposed posture (analogous to a catatonic stupor in humans). Rats are tested for induction of catalepsy in a dose-response test after oral administration of compounds.

d) CNS Penetration; In Vivo Brain Receptor Occupancy

In Vivo Binding. To determine the level of in vivo receptor occupancy, an in vivo receptor binding protocol is used. This procedure uses an appropriate radioligand to label the receptor of interest. For example, to measure both Dopamine D2 and 5-HT2A receptors in vivo, one can use $^3$H-N-methyl spiperone ($^3$H-NMSP), (Frost, et. al. 1987) The procedure uses rats (or mice) fasted overnight. To measure the effects of compounds on the receptors of interest, compounds are dosed, usually p.o. for example in 2 microliters/gram body weight in 0.25% Methocel suspension. The radiolabeled compound (in this example, $^3$H-NMSP) is administered by i.v. tail vein injection (10 microcuries label/200 gram rat). Time course experiments are used to determine the optimal time of binding for both the radiolabeled and unlabeled compound. These optimal time frames are used for all subsequent dose-response experiments. After the appropriate time frame of compound/radioligand exposure, the animals are sacrificed and the relevant brain regions dissected (frontal cortex for 5-HT2A and striatum for D2 receptors) and examined for their content of radioactivity. The level of non-specific binding is determined by examining a brain region known not to contain the receptor of interest (in this case the cerebellum) or by administering an excess of compound known pharmacologically to interact with the receptor.

REFERENCES

Arnt, J. Acta Pharmacol. et Toxicol. 1982: 51, 321-329.

Berridge M. J., Downes P. C., Hanley M. R. (1982) Lithium amplifies agonist-dependent phosphotidyinositol response in brain and salivary glands. Biochem. J., 206, 587-595.

Costall, B and Naylor, R J. Psychopharmacology. 1975: 43, 69-74.

Egan C. T., Herrick-Davis K., Miller K., Glennon R. A., and Teitler M. (1998) Agonist activity of LSD and lisuride at cloned 5-HT2A and 5-HT2C receptors. Psychopharmacology, 136, 409-414.

Fitzgerald L W, Conklin D S, Krause C M, Marshall A P, Patterson J P, Tran D P, Iyer G, Kostich W A, Largent B L, Hartig P R (1999) High-affinity agonist binding correlates with efficacy (intrinsic activity) at the human serotonin 5-HT2A and 5-HT2C receptors: evidence favoring the ternary complex and two-state models of agonist action. J. Neurochem., 72, 2127-2134.

Frost, J. J., Smith, A. C., Kuhar, M. J., Dannals, R. F., Wagner, H. N., 1987, In Vivo Binding of $^3$H-N-Methylspiperone to Dopamine and Serotonin Receptors. Life Sciences, 40:987-995.

Horlick, R. A., Sperle, K., Breth, L. A., Reid, C. C., Shen, E. S., Robbinds, A. K., Cooke, G. M., Largent, B. L. (1997) Rapid Generation of stable cell lines expressing corticotrophin-releasing hormone receptor for drug discovery. Protein Expr. Purif. 9, 301-308.

Lucki, I, Nobler, M. S., Frazer, A., 1984, Differential actions of serotonin antagonists on two behavioral models of serotonin receptor activation in the rat. J. Pharmacol. Exp. Ther. 228(1):133-139.

Dosage and Formulation

The serotonin agonist and serotonin antagonist compounds of this invention can be administered as treatment for the control or prevention of central nervous system disorders including obesity, anxiety, depression, psychosis, schizophrenia, sleep and sexual disorders, migraine and other conditions associated with cephalic pain, social phobias, and gastrointestinal disorders such as dysfunction of the gastrointestinal tract motility by any means that produces contact of the active agent with the agent's site of action, i.e., 5-HT2 receptors, in the body of a mammal. It can be administered by any conventional means available for use in conjunction with pharmaceuticals, either as an individual therapeutic agent or in a combination of therapeutic agents. It can be administered alone, but preferably is administered with a pharmaceutical carrier selected on the basis of the chosen route of administration and standard pharmaceutical practice.

The compounds of the present invention can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts.

The dosage administered will, of course, vary depending upon known factors, such as the pharmacodynamic characteristics of the particular agent and its mode and route of administration; the age, health and weight of the recipient; the nature and extent of the symptoms; the kind of concurrent treatment; the frequency of treatment; and the effect desired. By way of general guidance, a daily dosage of active ingredient can be expected to be about 0.001 to about 1000 milligrams per kilogram of body weight, with the preferred dose being about 0.01 to about 100 mg/kg; with the more preferred dose being about 0.1 to about 30 mg/kg. Advantageously, compounds of the present invention may be administered in a single daily dose, or the total daily dosage may be administered in divided doses of two, three, or four times daily.

Dosage forms of compositions suitable for administration contain from about 1 mg to about 100 mg of active ingredient per unit. In these pharmaceutical compositions the active ingredient will ordinarily be present in an amount of about 0.5-95% by weight based on the total weight of the composition. The active ingredient can be administered orally in solid dosage forms, such as capsules, tablets and powders, or in liquid dosage forms, such as elixirs, syrups and suspensions. It can also be administered parenterally, in sterile liquid dosage forms.

Gelatin capsules contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts, and sodium EDTA. In addition, parenteral solutions can contain preservatives, such as benzalkonium chloride, methyl- or propyl-paraben and chlorobutanol. Suitable pharmaceutical carriers are described in Remington's Pharmaceutical Sciences, supra, a standard reference text in this field.

Useful pharmaceutical dosage-forms for administration of the compounds of this invention can be illustrated as follows:

Capsules

A large number of unit capsules can be prepared by filling standard two-piece hard gelatin capsules each with 100 mg of powdered active ingredient, 150 mg of lactose, 50 mg of cellulose, and 6 mg magnesium stearic.

Soft Gelatin Capsules

A mixture of active ingredient in a digestible oil such as soybean oil, cottonseed oil or olive oil can be prepared and injected by means of a positive displacement pump into gelatin to form soft gelatin capsules containing 100 mg of the active ingredient. The capsules should then be washed and dried.

Tablets

A large number of tablets can be prepared by conventional procedures so that the dosage unit is 100 mg of active ingredient, 0.2 mg of colloidal silicon dioxide, 5 milligrams of magnesium stearate, 275 mg of microcrystalline cellulose, 11 mg of starch and 98.8 mg of lactose. Appropriate coatings may be applied to increase palatability or delay absorption.

Suspension

An aqueous suspension can be prepared for oral administration so that each 5 mL contain 25 mg of finely divided active ingredient, 200 mg of sodium carboxymethyl cellulose, 5 mg of sodium benzoate, 1.0 g of sorbitol solution, U.S.P., and 0.025 mg of vanillin.

Injectable

A parenteral composition suitable for administration by injection can be prepared by stirring 1.5% by weight of active ingredient in 10% by volume propylene glycol and water. The solution is sterilized by commonly used techniques.

What is claimed is:

1. A compound according to Formula (I):

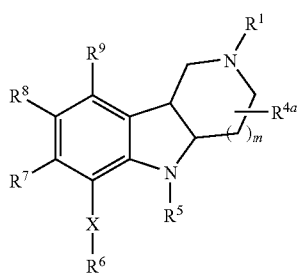

(I)

including all stereoisomers, and pharmaceutically acceptable salt forms thereof, wherein:

X is selected from the group consisting of —S—, —S(=O)—, —S(=O)$_2$— and —NR$^{10}$—;

R$^1$ is selected from the group consisting of
H,
C$_{3-7}$ cycloalkyl,
C$_{1-3}$ haloalkyl, and
C$_{1-4}$ alkyl substituted with 0-3 R$^2$;

R$^2$, at each occurrence, is independently selected from
halo, C$_{1-3}$ haloalkyl, C$_{1-4}$ alkoxy, C$_{1-4}$ alkyl,
C$_{2-4}$ alkenyl, C$_{2-4}$ alkynyl, C$_{3-6}$ cycloalkyl, and
aryl substituted with 0-5 R$^{21}$;

R$^{4a}$ is selected from the group consisting of H and C$_{1-4}$ alkyl;

R$^5$ is selected from the group consisting of H, C$_{1-4}$ alkyl;

R$^6$ is selected from the group consisting of —CF$_3$, C$_{1-6}$ alkyl, and aryl substituted with 0-5 R$^{21}$;

R$^7$, R$^8$, and R$^9$ are H;

R$^{10}$ is H or C$_{1-4}$ alkyl;

R$^{21}$, at each occurrence, is independently selected from
H, OH, halo, CF$_3$, SO$_2$R$^{45}$, NR$^{46}$R$^{47}$, CN, NO$_2$,
C$_{1-4}$ alkyl; C$_{2-8}$ alkenyl, C$_{2-8}$ alkynyl, C$_{1-4}$ alkoxy, and
C$_{1-4}$ haloalkyl;

R$^{45}$ is C$_{1-4}$ alkyl;

R$^{46}$, at each occurrence, is independently selected from H and C$_{1-4}$ alkyl;

R$^{47}$, at each occurrence, is independently selected from H, and C$_{1-4}$ alkyl; and m is 1.

2. A compound according to claim 1, wherein:

X is —S—;

R$^1$ is selected from
H, C$_{1-3}$ haloalkyl, C$_{3-6}$ cycloalkyl, and
C$_{1-4}$ alkyl substituted with 0-2 R$^2$;

R$^2$, at each occurrence, is independently selected from
halo, C$_{1-3}$ haloalkyl, C$_{1-4}$ alkoxy, C$_{1-4}$ alkyl,
C$_{3-6}$ cycloalkyl, and phenyl substituted with 0-5 R$^{21}$;

R$^5$ is H or C$_{1-4}$ alkyl;

R$^{21}$, at each occurrence, is independently selected from
H, OH, halo, CF$_3$, CN, NO$_2$,
C$_{1-4}$ alkyl, C$_{2-8}$ alkenyl, C$_{2-8}$ alkynyl, C$_{1-4}$ alkoxy, and
C$_{1-4}$ haloalkyl; and m is 1.

3. A compound according to claim 2, wherein:

R$^1$ is selected from H, CF$_3$, cyclopropyl, cyclobutyl, cyclopentyl, cyclohexyl, and C$_{1-4}$ alkyl substituted with 0-1 R$^2$;

R$^2$ is F, Cl, CH$_2$F, CHF$_2$, CF$_3$, methyl, ethyl, cyclopropyl, cyclobutyl, cyclopentyl, cyclohexyl, or phenyl;

R$^{4a}$ is H or methyl;

R$^5$ is H, methyl, or ethyl;

R$^6$ aryl substituted with 0-5 R$^{21}$; and

R$^{21}$, at each occurrence, is independently selected from
H, OH, halo, CF$_3$, and C$_{1-4}$ alkyl, C$_{1-4}$ alkoxy, and C$_{1-4}$ haloalkyl.

4. A compound according to claim 3, wherein:

R$^1$ is selected from H, methyl, ethyl, n-propyl, i-propyl, n-butyl, i-butyl, 1-methyl-propyl, 1-methyl-butyl, cyclobutyl-methyl, and benzyl; and R$^6$ is aryl substituted with 0-5 R$^{21}$.

5. A compound according to claim 4, wherein:

R$^1$ is methyl;

R$^5$ is H or methyl; and

R$^6$ is aryl substituted with 1-2 halo, CF$_3$, C$_{1-4}$ alkyl, and C$_{1-4}$ alkoxy.

6. A pharmaceutical composition comprising: at least one pharmaceutically acceptable carrier or diluent; and at least one compound according to claim 1.

7. A compound having the following Formula I, or a pharmaceutically acceptable salt thereof;

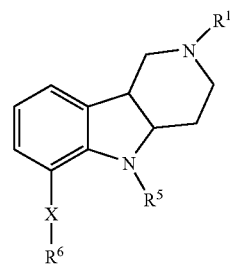

wherein X, R$^5$, R$^6$, and R$^1$ are defined as:

| X | R$^5$ | R$^6$ | R$^1$ |
|---|---|---|---|
| S | H | 4-Me—Ph— | Me |
| S | H | 4-F—Ph— | Me |
| S | H | 4-Cl—Ph— | Me |
| S | H | 4-Me—Ph— | H |
| NH | Me | 4-Me—Ph— | Me |
| S | H | 4-Me—Ph— | —(CH$_2$)$_3$C(=O)(4-F-phenyl) |
| S | Me | 4-Me—Ph— | Me |
| S | Me | 4-F—Ph— | Me |
| S | Me | 4-MeS—Ph— | Me |
| S | Me | 2-naphthyl | Me |
| S | H | Me | H |
| S | H | 2-Me—Ph— | H |
| S | H | 4-MeO—Ph— | H |
| S | H | 4-Br—Ph— | H |
| S | H | 4-MeO—Ph— | Me |
| S | H | 4-Br—Ph— | Me |
| S | H | 3-Cl—Ph— | Me |
| S | H | 2,5-diCl—Ph— | Me |
| S | H | 4-F—Ph— | Me |
| S | H | 4-Cl—Ph— | Me |
| S | Me | 4-Me—Ph— | H |
| S | Me | 4-Me—Ph— | cyclobutylmethyl |
| S | Me | 4-Me—Ph— | propyl |
| S | Me | 4-Me—Ph— | i-propyl |
| S | Me | 4-Me—Ph— | i-butyl |
| S | Me | 4-Me—Ph— | 1-Me-propyl |
| S | Me | 4-Me—Ph— | 1-Me-butyl |

-continued

| X | $R^5$ | $R^6$ | $R^1$ |
|---|---|---|---|
| S | Me | 4-Me—Ph— | butyl |
| S | Me | 4-Me—Ph— | benzyl |
| S | Me | 4-Me—Ph— | 4-pentenyl |
| S | H | 4-Me—Ph— | i-propyl |
| S | Me | 4-Et—Ph— | Me |
| S | Me | 4-iPr—Ph— | Me |
| S | Me | 4-CF$_3$—Ph— | Me |
| S | Me | 4-Br—Ph— | Me |
| S | Me | 1-naphthyl | Me |
| S | Me | 2-NH$_2$—Ph— | Me |
| S | Me | Ph | Me |

-continued

| X | $R^5$ | $R^6$ | $R^1$ |
|---|---|---|---|
| S | H | 3-Cl-4-F—Ph— | Me |
| S | H | 1-naphthyl | Me |
| S | Me | 4-Cl—Ph— | Me |
| S | H | 4-Me—Ph— | H |
| S | H | Me | —(CH$_2$)$_3$C(=O)(4-F-phenyl) |
| S | Me | 4-Me—Ph— | Me |
| S(=O) | H | Me | H. |

\* \* \* \* \*

UNITED STATES PATENT AND TRADEMARK OFFICE
CERTIFICATE OF CORRECTION

PATENT NO.       : 7,592,454 B2
APPLICATION NO.  : 11/104933
DATED            : September 22, 2009
INVENTOR(S)      : Taekyu Lee et al.

Page 1 of 1

It is certified that error appears in the above-identified patent and that said Letters Patent is hereby corrected as shown below:

Claim 1:
   Column 47, line 40, change "H," to -- H and --.

Claim 3:
   Column 48, line 9, after "$R^6$, insert -- is --.
   Column 48, line 26, change ";" to -- : --.

Signed and Sealed this
Eighth Day of November, 2011

David J. Kappos
*Director of the United States Patent and Trademark Office*